(12) United States Patent
Salvemini et al.

(10) Patent No.: US 11,919,895 B2
(45) Date of Patent: Mar. 5, 2024

(54) GPR183 ANTAGONISTS FOR THE TREATMENT OF PAIN

(71) Applicant: Saint Louis University, St. Louis, MO (US)

(72) Inventors: Daniela Salvemini, Chesterfield, MO (US); Christopher K. Arnatt, Manchester, MO (US)

(73) Assignee: Saint Louis University, St. Louis, MO (US)

( * ) Notice: Subject to any disclaimer, the term of this patent is extended or adjusted under 35 U.S.C. 154(b) by 327 days.

(21) Appl. No.: 17/080,247

(22) Filed: Oct. 26, 2020

(65) Prior Publication Data

US 2021/0122750 A1 Apr. 29, 2021

Related U.S. Application Data

(60) Provisional application No. 62/925,866, filed on Oct. 25, 2019.

(51) Int. Cl.
| | | |
|---|---|---|
| *C07D 471/04* | (2006.01) | |
| *A61P 23/00* | (2006.01) | |
| *A61P 25/02* | (2006.01) | |
| *C07D 217/06* | (2006.01) | |
| *C07D 295/135* | (2006.01) | |

(52) U.S. Cl.
CPC ............ *C07D 471/04* (2013.01); *A61P 23/00* (2018.01); *A61P 25/02* (2018.01); *C07D 217/06* (2013.01); *C07D 295/135* (2013.01)

(58) Field of Classification Search
CPC ............... C07D 471/04; C07D 271/06; C07D 295/135; A61P 25/02; A61P 23/00
See application file for complete search history.

(56) References Cited

U.S. PATENT DOCUMENTS

| | | | | |
|---|---|---|---|---|
| 3,296,261 A * | 1/1967 | Partyka | ................ | C07D 239/56 544/123 |
| 4,548,942 A * | 10/1985 | Shroot | ................... | A61K 31/70 514/859 |
| 2005/0004126 A1 * | 1/2005 | Andrianjara | ......... | C07D 513/04 514/249 |
| 2005/0154230 A1 * | 7/2005 | Yura | ....................... | A61P 25/04 564/52 |

FOREIGN PATENT DOCUMENTS

| | | | | |
|---|---|---|---|---|
| DE | 4304794 A1 * | 8/1994 | ............ | B60R 1/025 |
| WO | WO92/08719 | * 5/1992 | | |

OTHER PUBLICATIONS

Copeland, 65 J. Am. Chem. Soc. 1072-5 (1943) (Year: 1943).*
Billman, 66 J. Am. Chem. Soc. 540-1 (1944). (Year: 1944).*
Osbond, J. Chem. Soc. 3464-75 (1951) (Year: 1951).*

* cited by examiner

*Primary Examiner* — Timothy R Rozof
(74) *Attorney, Agent, or Firm* — Stinson LLP

(57) ABSTRACT

Disclosed herein are compositions and methods for treating neuropathic pain in a subject in need thereof. Compositions disclosed herein are GPR183 antagonists. The methods include administering to a subject in need thereof a therapeutically effective amount of a GPR183 antagonist.

2 Claims, 18 Drawing Sheets
(16 of 18 Drawing Sheet(s) Filed in Color)
Specification includes a Sequence Listing.

| Compound | Enamine Code | Structure | IC$_{50}$ (nM) |
|---|---|---|---|
| SAE-1 | Z2241108387 | 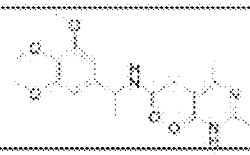 | 8.31 |
| SAE-10 | Z230959340 | 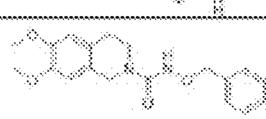 | 13.9 |
| SAE-14 | Z966709080 | 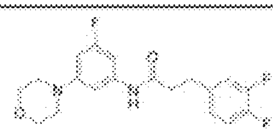 | 28.5 |

SEQUENCE LISTING

```
<160> NUMBER OF SEQ ID NOS: 3

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
gaagcuucgu uucucuaau                                                    19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
gcaggaggcu gaaaggauu                                                    19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
gucaguguau cgauuucua                                                    19
```

GPR183 ANTAGONISTS FOR THE TREATMENT OF PAIN

INCORPORATION OF SEQUENCE LISTING

A paper copy of the Sequence Listing and a computer readable form of the Sequence Listing containing the file named "SLU19-030_ST25.txt", which is 844 bytes in size as Measured in MICROSOFT WINDOWS EXPLORER®), are provided herein and are herein incorporated by reference. This Sequence Listing consists of SEQ ID NOS:1-3.

BACKGROUND OF THE DISCLOSURE

The present disclosure generally relates to medicine. More particularly, the present disclosure is directed to compositions and methods for preventing and treating pain using GPR183 antagonists.

Pain is an unpleasant feeling often caused by intense or damaging stimuli. The International Association for the Study of Pain's widely used definition states: "Pain is an unpleasant sensory and emotional experience associated with actual or potential tissue damage, or described in terms of such damage." Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Neuropathic pain conditions arising from nervous system injuries due to trauma, disease (i.e., diabetes) or neurotoxins (i.e. chemotherapy) are severe, debilitating and difficult to treat. Opioids are widely used to treat chronic pain but limited by severe side effects and strong abuse liability. With over 15-20 million people in the US suffering neuropathic pain and a profound annual economic burden for treatment, there is a high priority for developing novel non-opioid based analgesics.

GPR183 (EBI2, Epstein-Barr virus-induced G-protein coupled receptor 2) is a $G\alpha_i$-coupled protein that when activated by $7\alpha,25$-dihydroxycholesterol ($7\alpha,25$-OHC) can inhibit adenylate cyclase activity, activate extracellular signal-regulated kinase (ERK) and p38 pathways and trigger serum response element binding. These pathways are crucial to persistent pain sensitization.

GPR183 was originally identified in B-cells as the most upregulated gene in response to Epstein-Barr virus infection (Birkenbach et al., 1993). This receptor has been found in multiple human tissues including brain but was found most abundantly in lymphoid organs and is most highly expressed on B-cells (Rosenkilde et al., 2006). Similar patterns of expression have been found in rodents (Lein et al., 2007) and the human receptor sequence shares 88% homology with the rodent sequences, according to NCBI Blast (Boratyn et al., 2013). GPR183 is important for the positioning of immune cells, particularly B-cells, within lymphoid tissues, such as the spleen, for the launching of T-cell dependent antibody responses (Gatto et al., 2009; Pereira et al., 2009). GPR183 knockout mice are viable and have a normal gross phenotype: these mice have normal numbers of B cells and T cells with no defect in B-cell localization within the spleen (Pereira et al., 2009). Besides its role in regulating immune cell migration, GPR183 has been linked to metabolic diseases, multiple sclerosis, and cancer; accordingly, GPR183 has been proposed to represent a potential target for several diseases ranging from inflammation to cancer (Sun and Liu, 2015).

The role of GPR183 in the central nervous system (CNS) is still under investigation and its role in the context of pain is not known. At the cellular level, GPR183 has only been reported to be expressed in astrocytes within the CNS (Rutkowska et al., 2015). Other studies have found microglia are able to produce and release $7\alpha,25$-OHC, but it was not explored whether microglia respond to the GPR183 ligand (Mutemberezi et al., 2018). GPR183 is $G\alpha i$-coupled and when activated by $7\alpha,25$-OHC, it can inhibit adenylate cyclase activity, increase phosphorylation of extracellular signal-regulated kinase (ERK) and p38 and trigger serum response element (SRE) activity (Rosenkilde et al., 2006; Benned-Jensen et al., 2011; Hannedouche et al., 2011; Liu et al., 2011; Benned-Jensen et al., 2013). Activation of these pathways in CNS glia as well as in dorsal root ganglia (DRG) neurons is crucial to the persistent pain sensitization and to pain chronification (Ji et al., 2009; Gomez et al., 2018).

Commercially available GPR183 antagonists are limited to a couple of compounds with chemical properties that question in vivo utility (Ardecky et al., 2010).

Accordingly, there exists a need to develop new compositions and methods for treating pain. To address this need, drug discovery efforts identified novel GPR183 antagonists for use in exploring the roles of GPR183 in neuropathic pain states and led to the identification of several potent small-molecule selective GPR183 antagonists that were active in a rodent model of neuropathic pain caused by chronic constriction of the sciatic nerve (Bennett and Xie, 1988).

BRIEF DESCRIPTION OF THE DISCLOSURE

The present disclosure is generally related to compositions and methods for treating pain. More particularly, the present disclosure is directed to GPR183 antagonists and their use in methods for treating pain.

In one aspect, the present disclosure is directed to a GPR183 antagonist.

In one aspect, the present disclosure is directed to a method for treating pain in a subject in need thereof, the method comprising: administering to the subject in need thereof a therapeutically effective amount of a GPR83 antagonist.

BRIEF DESCRIPTION OF THE DRAWINGS

The patent or application file contains at least one drawing executed in color. Copies of this patent or patent application publication with color drawings will be provided by the Office upon request and payment of the necessary fee. The disclosure will be better understood, and features, aspects and advantages other than those set forth above will become apparent when consideration is given to the following detailed description thereof. Such detailed description makes reference to the following drawings, wherein:

FIG. 9A. Mechano-allodynia in male rats following CCI or sham surgery (n=4/group). FIG. 9B. Gpr183 expression in the ipsilateral DH-SC from male rats on day 10 post CCI or sham surgery (n=4). FIG. 9C depicts the quantification and FIG. 9D depicts a representative image of Gpr183 expression in the spinal cord on day 10 CCI or sham surgery by RNASCOPE® analyses. Image was stitched (x, y, and z; original magnification of 40× and axial depth of 6 m) composite of spinal cord probed for Gfap (green). Gpr183 (red) and DAPI (blue). Signal was dilated by 3 pixel diameters for display purposes; box=area of quantification; ipsi=ipsilateral and contra=contralateral side to injury. Scale bar=200 µm. Data are mean±SD (FIG. 9A) or median and analyzed by two-tailed (FIG. 9C), two-way repeated measures ANOVA (RM-ANOVA) with Bonferroni comparisons (FIG. 9A) or paired Student's t test FIG. 9C). *P<0.05 vs. Sham or #P<0.05 vs. Contra.

FIGS. 10A-10C depict representative images (ipsilateral) with magnified inset to show detail and FIGS. 10D-10F depict the quantification of the RNASCOPE® signal for Gpr183 (yellow) and its colocalization with Aif1 (microglia; n=10; magenta; FIGS. 10A, 10D), Gfap (astrocytes; n=10; magenta; FIGS. 10B, 10E) or Rbfox3 (neurons; n=8; magenta; FIGS. 10C, 10F) in superficial DH-SC (regions are marked by white box in FIG. 9D). Signal for lineage markers (magenta) was dilated by 0.5 pixel diameters to create a selection region that was applied to quantify Gpr183 for that cell lineage. Scale bar=50 µm. Data are median and analyzed by two-tailed, paired Student's t test. *P<0.05 vs. Contra.

FIG. 12A depicts workflow of in silico modeling. FIG. 12B depicts structures, enamine codes, and $IC_{50}$'s of tested compounds. FIG. 12C depicts calcium mobilization dose response for HL-60 cells to 7α,25-OHC. Error bars represent mean & SEM for n=5. FIG. 12D depicts dose-response of HL-60 cells to SAE-1, SAE-10, and SAE-14 inhibition of calcium mobilization induced by 7α,25-OHC ($EC_{80}$ 209 nM). Error bars represent mean±SEM for n=4. FIG. 12E depicts calcium mobilization dose response of HL-60 cells treated with or without Gpr183-targeting siRNA to 7α,25-OHC (n=3). FIG. 12F depicts dose response of HL-60 cells treated with or without Gpr183-targeting siRNA to SAE-14 inhibition of calcium mobilization induced by 7α,25-OHC ($EC_{80}$ 209 nM). Data are mean±SEM for n=3.

FIG. 14A depicts acute intrathecal injection of 7α,25-OHC (24 nM, n=6; 72 nM, n=6 and 240 nM, n=14) or its synthetic analog (SLUPP-1492; 615 nM, n=8) induced mechano-allodynia in male and female mice (data combined) in a dose-dependent manner. FIG. 14B depicts intrathecal administration of 7α,25-OHC (240 nM) and SLUPP-1492 (615 nM) also induced time-dependent development of cold-allodynia (n=6/group). Pre-treatment by intrathecal administration of SAE-14 (3 µM mechano n=9/cold n=8; 1 µM n=9; 0.3 µM n=9), but not vehicle (mechano n=9/cold n=6), dose-dependently prevented the development of mechano-allodynia (FIG. 14C) and cold-allodynia (FIG. 14D) induced by 7α,25-OHC (480 nM) in male and female mice. Data are mean±SD and analyzed by two-way ANOVA with Dunnett's comparison. *p<0.05 vs 0 hours; †p<0.05 vs Veh group.

DETAILED DESCRIPTION

Figure 1:
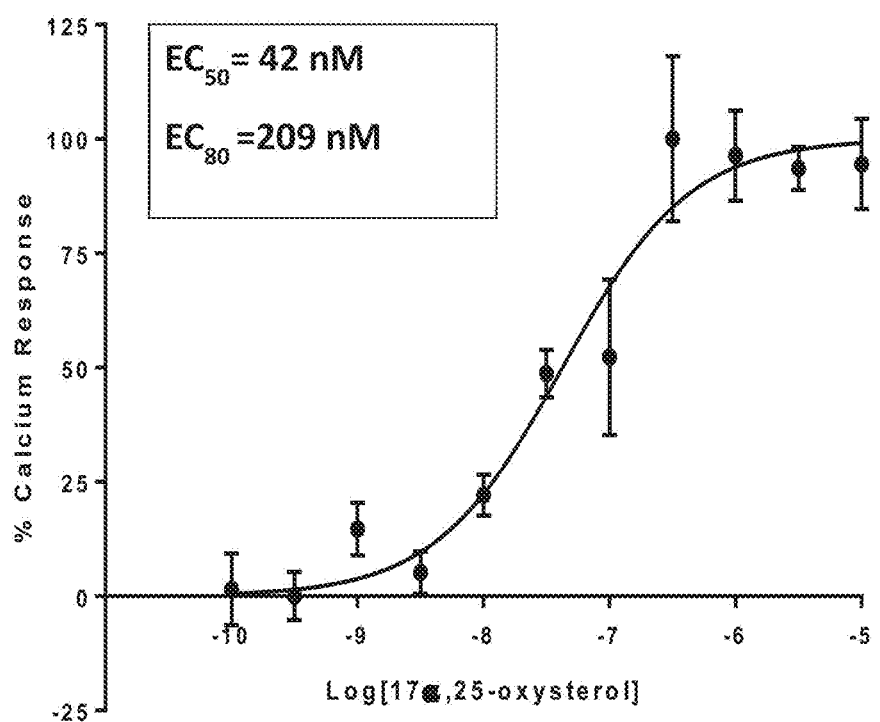
FIG. 1 depicts 7-alpha,25-oxysterol induced calcium mobilization in HL-60 cells.
Figure 2:
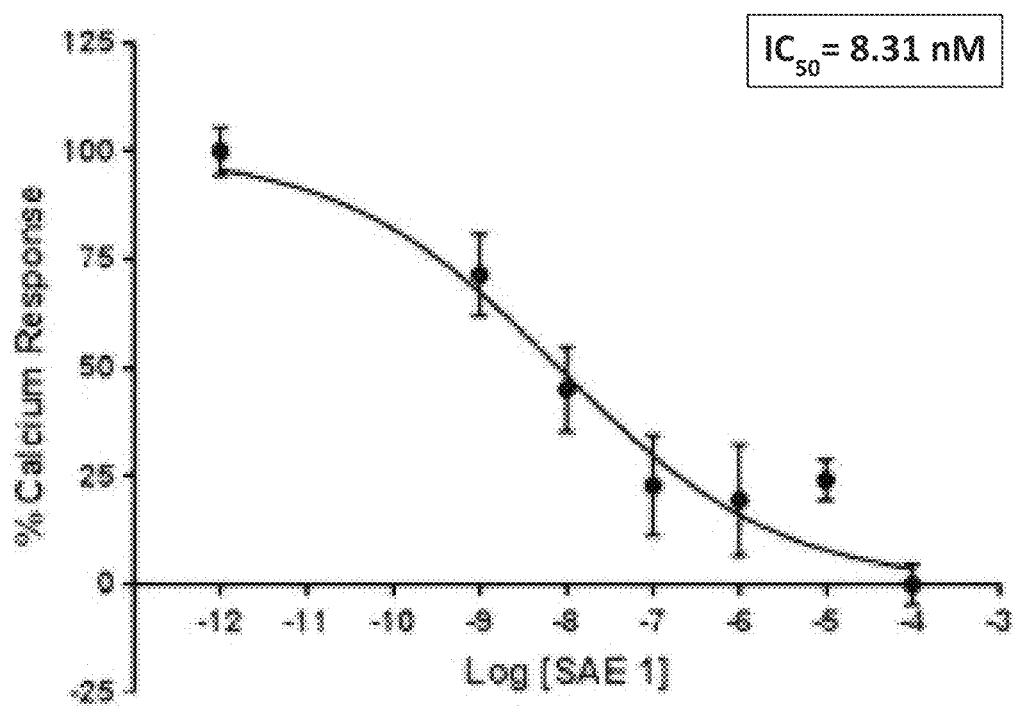
FIG. 2 depicts initial dose curves of SAE-1.
Figure 3:
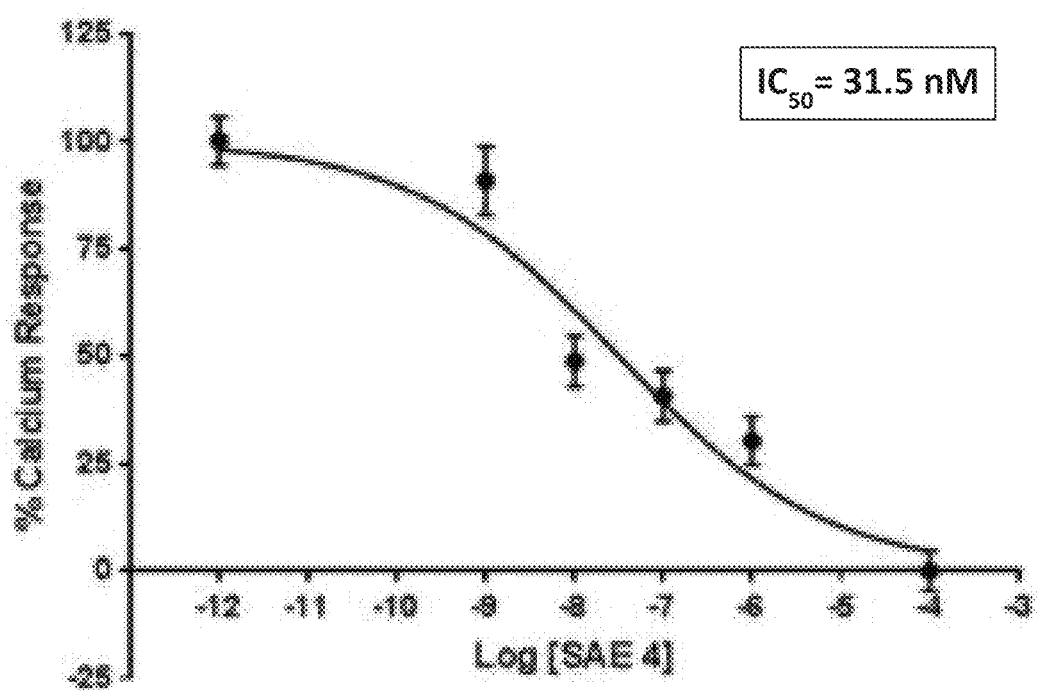
FIG. 3 depicts initial dose curves of SAE-4.
Figure 4:
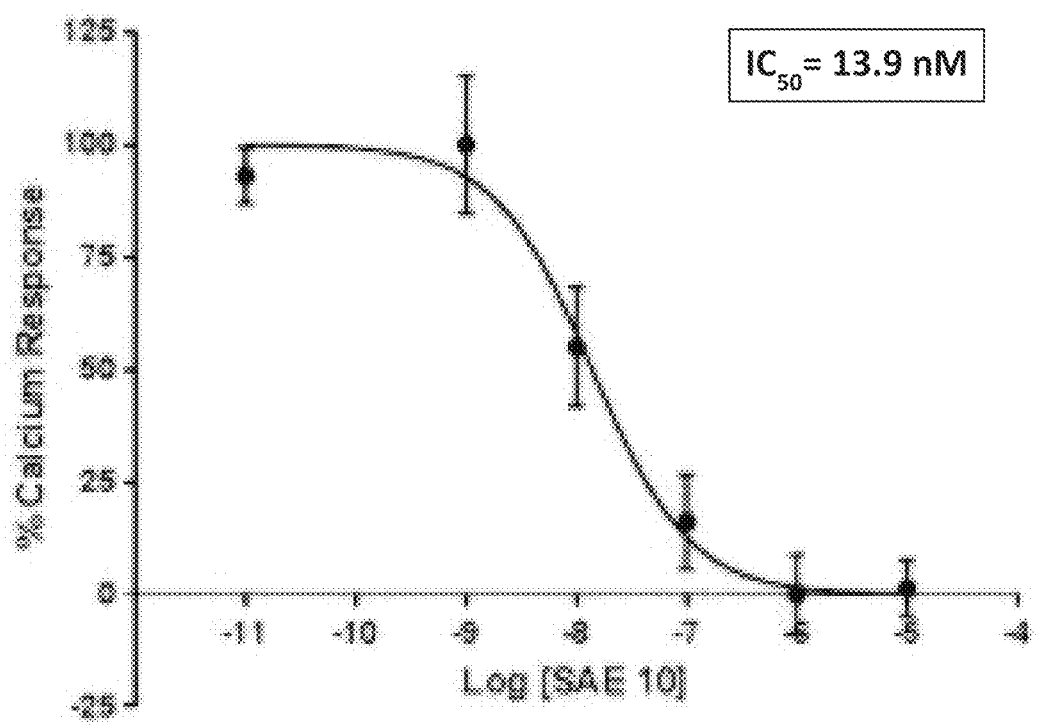
FIG. 4 depicts initial dose curves of SAE-10.
Figure 5:
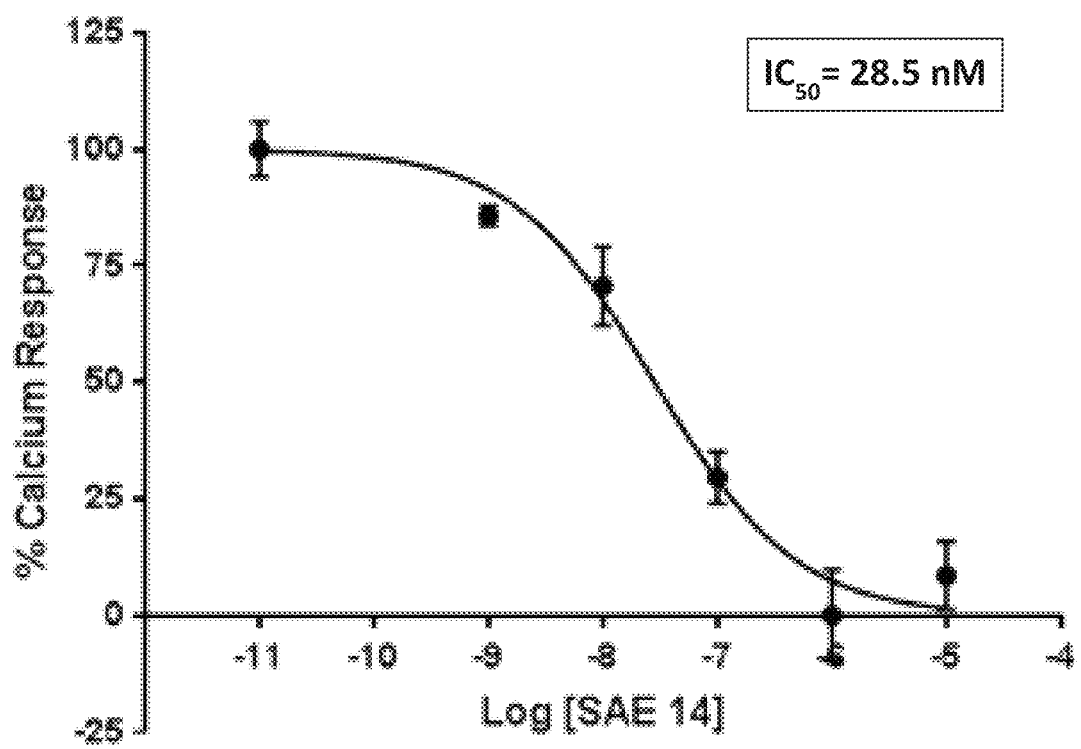
FIG. 5 depicts initial dose curves of SAE-14.
Figure 6A:
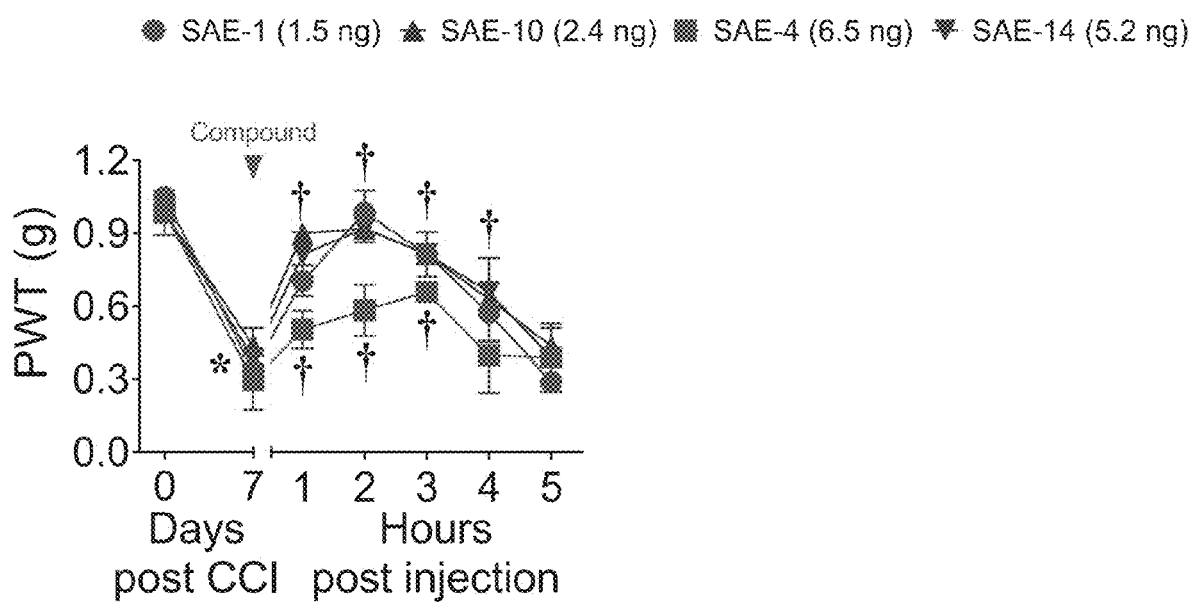
FIGS. 6A & 6B depict intrathecal injection (5 µl) of GPR83 antagonists reversal of CCI-induced neuropathic pain behaviors ipsilateral to injury (FIG. 6A) No effects on behavior on the contralateral side (FIG. 6B). Mean±SD; n=2/group; RM-ANOVA with Dunnett's comparisons. *P<0.05 vs. day 0 and †P<0.05 vs. day 7.
Figure 6B:
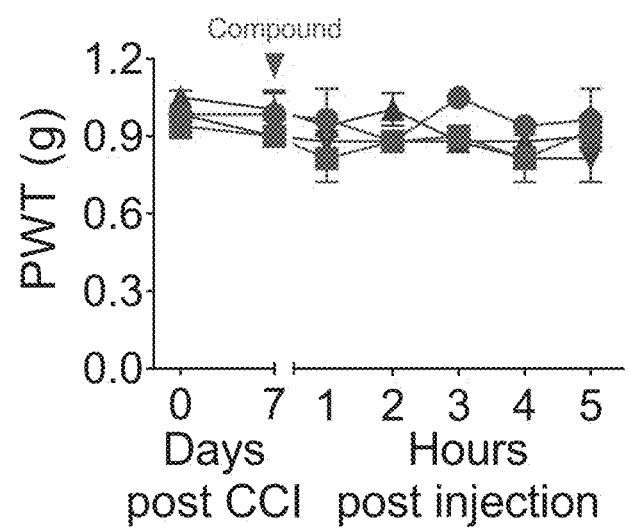
Figure 7A:
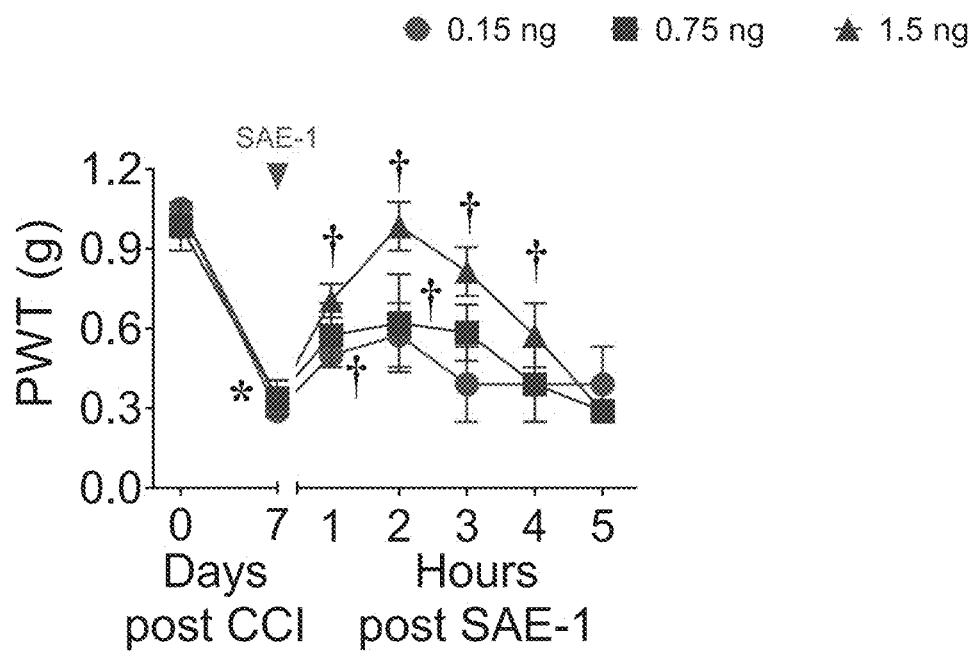
FIGS. 7A & 7B depict intrathecal injection (5 µl) of SAE-1 reversal of CCI-induced neuropathic pain behaviors ipsilateral to injury in a time- and dose-dependent manner (FIG. 7A). No effects on behaviors on the contralateral side (FIG. 7B). Mean±SD; n=2/group; RM-ANOVA with Dunnett's comparisons. *P<0.05 vs. day 0 and †P<0.05 vs. day 7.
Figure 7B:
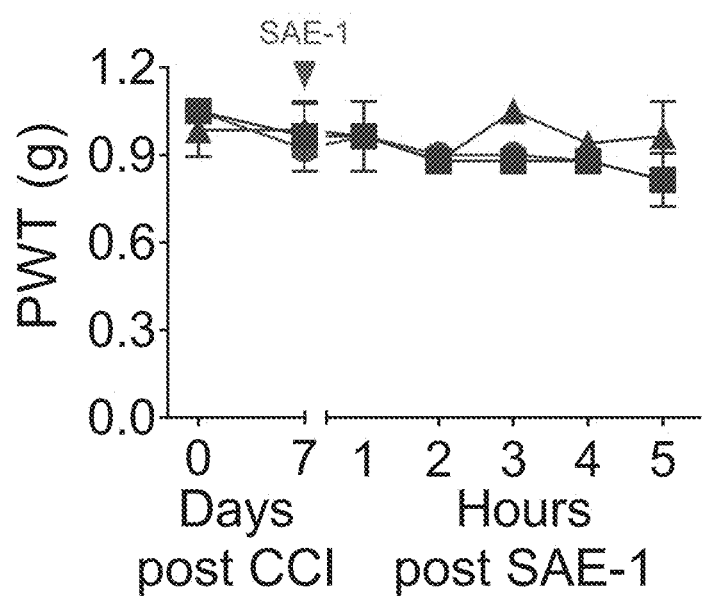
Figure 8A:
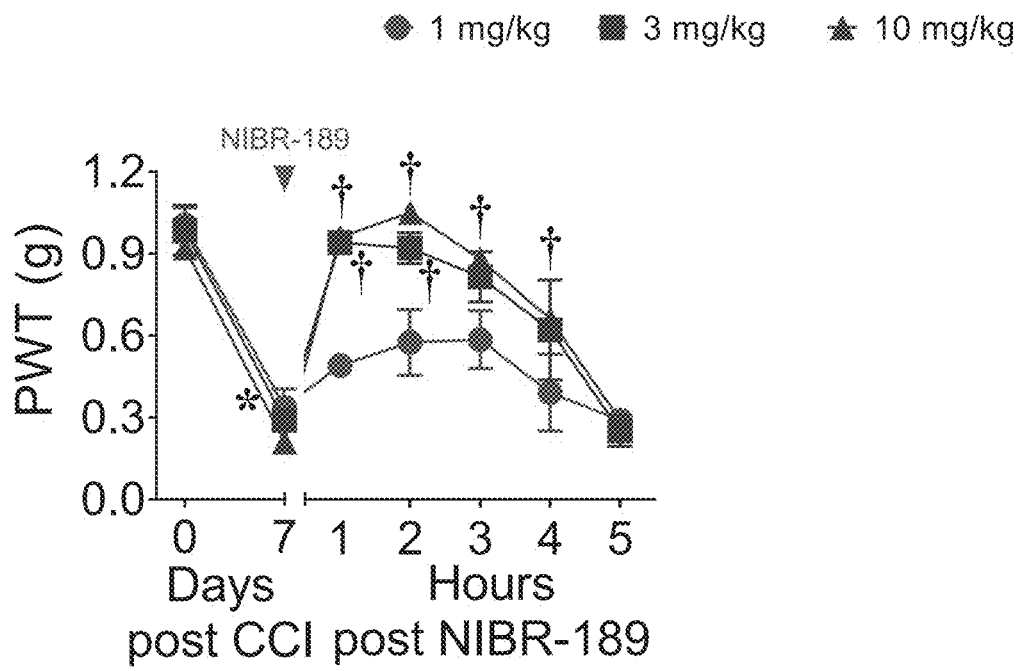
FIGS. 8A & 8B depict intrathecal injection (5 µl) of NIBR-189 in DMSO reversal of CCI-induced neuropathic pain behaviors ipsilateral to injury in a time- and dose-dependent manner (FIG. 8A). No effects on behaviors on the contralateral side (FIG. 8B). Mean±SD; n=2/group; RM-ANOVA with Dunnett's comparisons. *P<0.05 vs. day 0 and †P<0.05 vs. day 7.
Figure 8B:
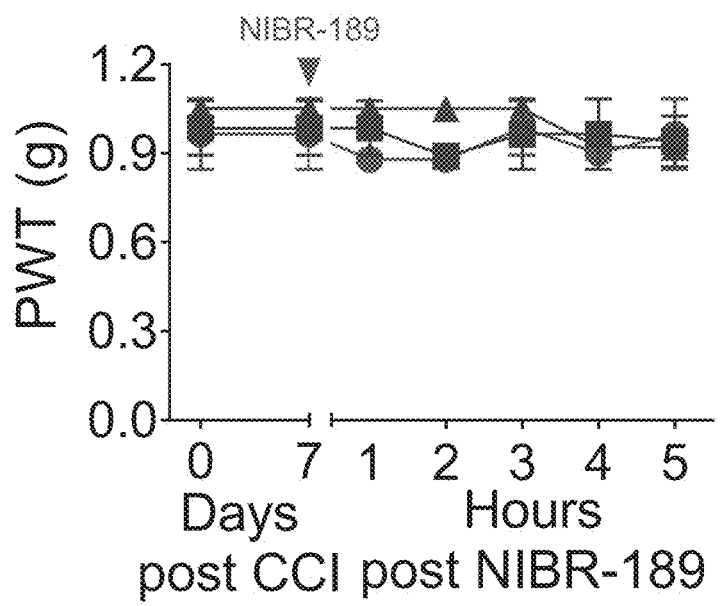

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Disclosed are compositions and methods for treating pain.

In one aspect, the present disclosure is directed to a GPR183 antagonist.

The GPR183 antagonist antagonist is a compound having a formula that includes at least two aromatic and/or heterocycles, linked together by a 4-atom linker. In some embodiments, the 4-atom linker includes an amide and three additional atoms, the three atoms being selected from oxygen and carbon.

In one aspect, the GPR183 antagonist has formula (I)

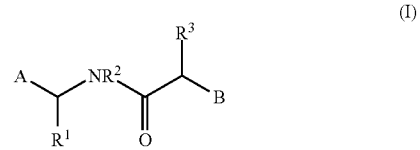

wherein A is selected from an aromatic ring, a heterocycle, a fused ring system, and a multiple ring system;

and wherein B is selected from an aromatic ring and a heterocycle; and wherein $R^1$ and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; and $R^2$ is selected from H, —$CH_3$, —$CH_2CH_3$, —$CF_3$; or a pharmaceutically acceptable salt thereof.

In one aspect, the GPR183 antagonist has formula (I)

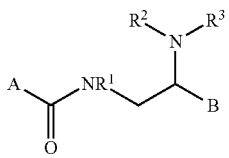
(II)

wherein A is selected from an aromatic ring, a heterocycle, a fused ring system, and a multiple ring system; wherein B is selected from an aromatic ring and a heterocycle; and wherein $R^1$ is selected from H, —$CH_3$, —$CH_2CH_3$, —$CF_3$; and $R^2$ and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; or a pharmaceutically acceptable salt thereof.

In one aspect, the GPR183 antagonist has formula (III)

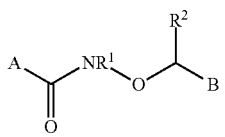
(III)

wherein A is selected from an aromatic ring, a heterocycle, a fused ring system, and a multiple ring system; wherein B is selected from an aromatic ring and a heterocycle; and wherein $R^1$ is selected from H, —$CH_3$, —$CH_2CH_3$, —$CF_3$; and $R^2$ is selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; or a pharmaceutically acceptable salt thereof.

In one aspect, the GPR183 antagonist has formula (IV)

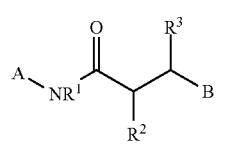
(IV)

wherein A is selected from an aromatic ring, a heterocycle, a fused ring system, and a multiple ring system; wherein B is selected from an aromatic ring and a heterocycle; and wherein $R^1$ is selected from H, —$CH_3$, —$CH_2CH_3$, —$CF_3$; and $R^2$ and $R^3$ are independently selected from is selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; or a pharmaceutically acceptable salt thereof.

In one aspect, the GPR183 antagonist has formula (V)

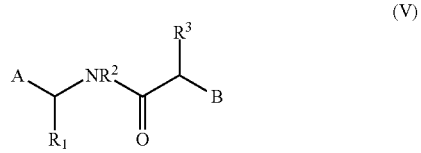
(V)

wherein A is selected from an aromatic ring, a heterocycle, a fused ring system, and a multiple ring system; wherein B is selected from an aromatic ring and a heterocycle; and wherein $R^1$ and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; and $R^2$ is selected from H, —$CH_3$, —$CH_2CH_3$, —$CF_3$; or a pharmaceutically acceptable salt thereof.

In one aspect, the GPR183 antagonist has formula (VI)

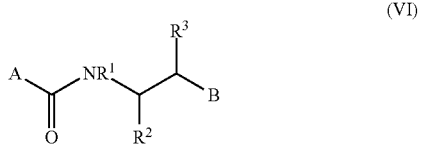
(VI)

wherein A is selected from an aromatic ring, a heterocycle, a fused ring system, and a multiple ring system; wherein B is selected from an aromatic ring and a heterocycle; and wherein $R^1$ is selected from H, —$CH_3$, —$CH_2CH_3$, —$CF_3$; and $R^2$ and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; or a pharmaceutically acceptable salt thereof.

In one aspect, the GPR183 antagonist has formula (VII)

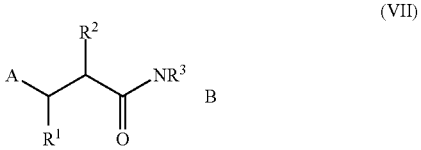
(VII)

wherein A is selected from an aromatic ring, a heterocycle, a fused ring system, and a multiple ring system; wherein B is selected from an aromatic ring and a heterocycle; and wherein $R^1$ and $R^2$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; and $R^3$ is selected from H, —$CH_3$, —$CH_2CH_3$, —$CF_3$; or a pharmaceutically acceptable salt thereof.

In one aspect, the GPR183 antagonist has formula (VIII)

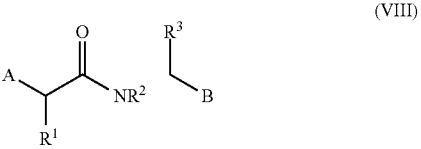
(VIII)

wherein A is selected from an aromatic ring, a heterocycle, a fused ring system, and a multiple ring system; wherein B is selected from an aromatic ring and a heterocycle; and wherein $R^1$ and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; and $R^2$ is selected from H, —$CH_3$, —$CH_2CH_3$, —$CF_3$; or a pharmaceutically acceptable salt thereof.

In one aspect, the GPR183 antagonist has formula (IX)

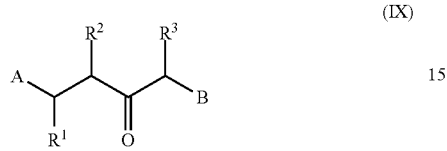

wherein A is selected from an aromatic ring, a heterocycle, a fused ring system, and a multiple ring system; wherein B is selected from an aromatic ring and a heterocycle; and wherein $R^1$, $R^2$, and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; or a pharmaceutically acceptable salt thereof.

In one aspect, the GPR183 antagonist has formula (X)

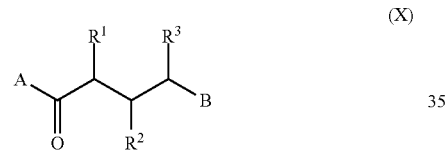

wherein A is selected from an aromatic ring, a heterocycle, a fused ring system, and a multiple ring system; wherein B is selected from an aromatic ring and a heterocycle; and wherein $R^1$, $R^2$, and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; or a pharmaceutically acceptable salt thereof.

In one aspect, the GPR183 antagonist has formula (XI)

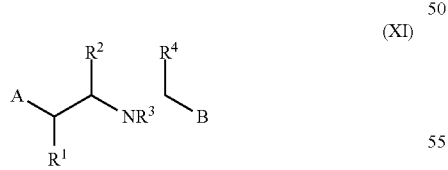

wherein A is selected from an aromatic ring, a heterocycle, a fused ring system, and a multiple ring system; wherein B is selected from an aromatic ring and a heterocycle; and wherein $R^1$, $R^2$, and $R^4$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; and $R^2$ is selected from H, —$CH_3$, —$CH_2CH_3$, —$CF_3$; or a pharmaceutically acceptable salt thereof.

In one aspect, the GPR183 antagonist has formula (XII)

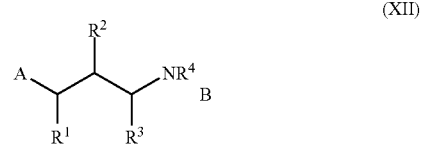

wherein A is selected from an aromatic ring, a heterocycle, a fused ring system, and a multiple ring system; wherein B is selected from an aromatic ring and a heterocycle; and wherein $R^1$, $R^2$, and $R^3$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; and $R^4$ is selected from H, —$CH_3$, —$CH_2CH_3$, —$CF_3$; or a pharmaceutically acceptable salt thereof.

In one aspect, the GPR183 antagonist has formula (XIII)

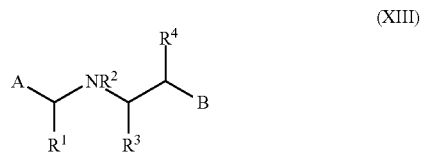

wherein A is selected from an aromatic ring, a heterocycle, a fused ring system, and a multiple ring system; wherein B is selected from an aromatic ring and a heterocycle; and wherein $R^1$, $R^3$ and $R^4$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; and $R^2$ is selected from H, —$CH_3$, —$CH_2CH_3$, —$CF_3$; or a pharmaceutically acceptable salt thereof.

In one aspect, the GPR183 antagonist has formula (XIV)

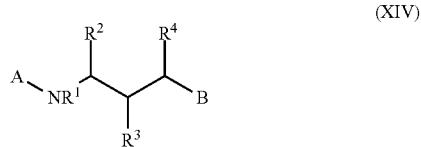

wherein A is selected from an aromatic ring, a heterocycle, a fused ring system, and a multiple ring system; wherein B is selected from an aromatic ring and a heterocycle; and wherein $R^2$. R and $R^4$ are independently selected from H, —$CH_3$, —$CH_2CH_3$, —$CH_2CH_2CH_3$, —$CH(CH_3)_2$, —$CF_3$, —OH, —$OCH_3$, $OCH_2CH_3$, —$NH_2$, —$N(CH_3)_2$, —$N(CH_3)_3$, and —$N(CH_2CH_3)_2$; $R^1$ is selected from H, —$CH_3$, —$CH_2CH_3$, —$CF_3$; or a pharmaceutically acceptable salt thereof.

In one aspect, the GPR183 antagonist has formula (XV)

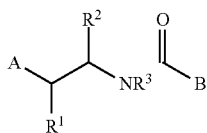
(XV)

wherein A is selected from an aromatic ring, a heterocycle, a fused ring system, and a multiple ring system; wherein B is selected from an aromatic ring and a heterocycle; and wherein R$^1$ and R$^2$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; R$^3$ is selected from H, —CH$_3$, —CH$_2$CH$_3$, —CF$_3$; or a pharmaceutically acceptable salt thereof.

In one aspect, the GPR183 antagonist has formula (XVI)

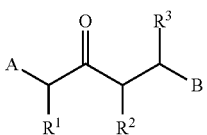
(XVI)

wherein A is selected from an aromatic ring, a heterocycle, a fused ring system, and a multiple ring system; wherein B is selected from an aromatic ring and a heterocycle; and wherein R$^1$, R$^2$, and R$^3$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; or a pharmaceutically acceptable salt thereof.

In one aspect, the present disclosure is directed to a method for treating pain by administering to a subject in need thereof a therapeutically effective amount of a GPR183 antagonist.

Suitable GPR183 antagonists are selected from formula (I), formula (II), formula (III), formula (IV), formula (V), formula (VI), formula (VII), formula (VIII), formula (IX), formula (X), formula (XI), formula (XII), formula (XIII), formula (XIV), formula (XV), and formula (XVI):

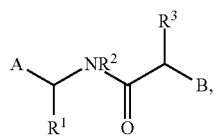
(I)

wherein A is selected from an aromatic ring, a heterocycle, a fused ring system, and a multiple ring system; and wherein B is selected from an aromatic ring and a heterocycle; and wherein R$^1$ and R$^3$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; and R$^2$ is selected from H, —CH$_3$, —CH$_2$CH$_3$, —CF$_3$; or a pharmaceutically acceptable salt thereof;

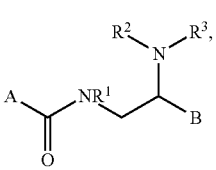
(II)

wherein A is selected from an aromatic ring, a heterocycle, a fused ring system, and a multiple ring system; wherein B is selected from an aromatic ring and a heterocycle; and wherein R$^1$ is selected from H, —CH, —CH$_2$CH$_3$, —CF$_3$; and R$^2$ and R$^3$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; or a pharmaceutically acceptable salt thereof;

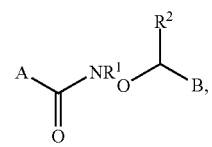
(III)

wherein A is selected from an aromatic ring, a heterocycle, a fused ring system, and a multiple ring system; wherein B is selected from an aromatic ring and a heterocycle; and wherein R$^1$ is selected from H, —CH$_3$, —CH$_2$CH$_3$, —CF$_3$; and R$^2$ is selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$ and —N(CH$_2$CH$_3$)$_2$; or a pharmaceutically acceptable salt thereof;

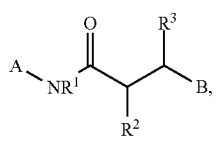
(IV)

wherein A is selected from an aromatic ring, a heterocycle, a fused ring system, and a multiple ring system; wherein B is selected from an aromatic ring and a heterocycle; and wherein R$^1$ is selected from H, —CH$_3$, —CH$_2$CH$_3$, —CF$_3$; and R$^2$ and R$^3$ are independently selected from is selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; or a pharmaceutically acceptable salt thereof;

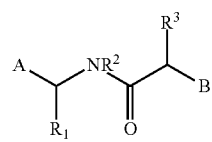
(V)

wherein A is selected from an aromatic ring, a heterocycle, a fused ring system, and a multiple ring system;

wherein B is selected from an aromatic ring and a heterocycle; and wherein R¹ and R³ are independently selected from H, —CH₃, —CH₂CH₃, —CH₂CH₂CH₃, —CH(CH₃)₂, —CF₃, —OH, —OCH₃, OCH₂CH₃, —NH₂, —N(CH₃)₂, —N(CH₃)₃, and —N(CH₂CH₃)₂; and R² is selected from H, —CH₃, —CH₂CH₃, —CF₃; or a pharmaceutically acceptable salt thereof;

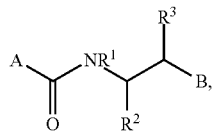
(VI)

wherein A is selected from an aromatic ring, a heterocycle, a fused ring system, and a multiple ring system; wherein B is selected from an aromatic ring and a heterocycle; and wherein R¹ is selected from H, —CH₃, —CH₂CH₃, —CF₃; and R² and R³ are independently selected from H, —CH₃, —CH₂CH₃, —CH₂CH₂CH₃, —CH(CH₃)₂, —CF₃, —OH—, —OCH₃, OCH₂CH₃, —NH₂, —N(CH₃)₂, —N(CH₃)₃, and —N(CH₂CH₃)₂; or a pharmaceutically acceptable salt thereof;

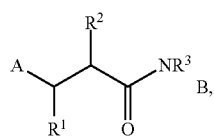
(VII)

wherein A is selected from an aromatic ring, a heterocycle, a fused ring system, and a multiple ring system; wherein B is selected from an aromatic ring and a heterocycle; and wherein R¹ and R² are independently selected from H, —CH₃, —CH₂CH₃, —CH₂CH₂CH₃, —CH(CH₃)₂, —CF₃, —OH, —OCH₃, OCH₂CH₃, —NH₂, —N(CH₃)₂, —N(CH₃)₃, and —N(CH₂CH₃)₂; and R³ is selected from H, —CH₃, —CH₂CH₃, —CF₃; or a pharmaceutically acceptable salt thereof;

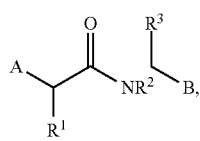
(VIII)

wherein A is selected from an aromatic ring, a heterocycle, a fused ring system, and a multiple ring system; wherein B is selected from an aromatic ring and a heterocycle; and wherein R¹ and R³ are independently selected from H, —CH₃, —CH₂CH₃, —CH₂CH₂CH₃, —CH(CH₃), —CF₃, —OH, —OCH₃, OCH₂CH₃, —NH₂, —N(CH₃)₂, —N(CH₃)₃, and —N(CH₂CH₃)₂; and R² is selected from H, —CH₃, —CH₂CH₃, —CF₃; or a pharmaceutically acceptable salt thereof;

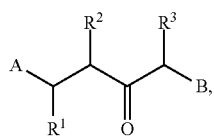
(IX)

wherein A is selected from an aromatic ring, a heterocycle, a fused ring system, and a multiple ring system; wherein B is selected from an aromatic ring and a heterocycle; and wherein R¹, R², and R³ are independently selected from H, —CH₃, —CH₂CH₃, —CH₂CH₂CH₃, —CH(CH₃)₂, —CF₃, —OH, —OCH, OCH₂CH₃, —NH₂, —N(CH₃)₂, —N(CH₃)₃, and —N(CH₂CH₃)₂; or a pharmaceutically acceptable salt thereof;

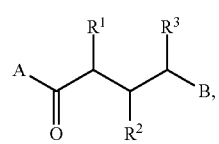
(X)

wherein A is selected from an aromatic ring, a heterocycle, a fused ring system, and a multiple ring system; wherein B is selected from an aromatic ring and a heterocycle; and wherein R¹, R², and R³ are independently selected from H, —CH₃, —CH₂CH₃, —CH₂CH₂CH₃, —CH(CH₃)₂, —CF₃, —OH, —OCH₃, OCH₂CH₃, —NH₂, —N(CH₃)₂, —N(CH₃)₃, and —N(CH₂CH₃)₂; or a pharmaceutically acceptable salt thereof;

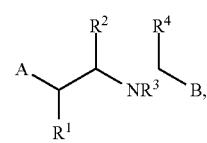
(XI)

wherein A is selected from an aromatic ring, a heterocycle, a fused ring system, and a multiple ring system; wherein B is selected from an aromatic ring and a heterocycle; and wherein R¹, R², and R⁴ are independently selected from H, —CH₃, —CH₂CH₃, —CH₂CH₂CH₃, —CH(CH₃)₂, —CF₃, —OH, —OCH₃, OCH₂CH₃, —NH₂, —N(CH₃)₂, —N(CH₃)₃, and —N(CH₂CH₃)₂; and R² is selected from H, —CH₃, —CH₂CH₃, —CF₃; or a pharmaceutically acceptable salt thereof;

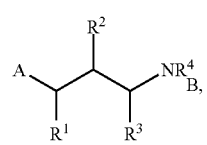
(XII)

wherein A is selected from an aromatic ring, a heterocycle, a fused ring system, and a multiple ring system; wherein B is selected from an aromatic ring and a heterocycle; and wherein $R^1$, $R^2$, and $R^3$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; and $R^4$ is selected from H, —CH$_3$, —CH$_2$CH$_3$, —CF$_3$; or a pharmaceutically acceptable salt thereof;

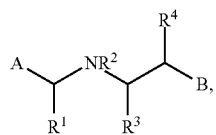

(XIII)

wherein A is selected from an aromatic ring, a heterocycle, a fused ring system, and a multiple ring system; wherein B is selected from an aromatic ring and a heterocycle; and wherein $R^1$, $R^3$ and $R^4$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; and $R^2$ is selected from H, —CH$_3$, —CH$_2$CH$_3$, —CF$_3$; or a pharmaceutically acceptable salt thereof;

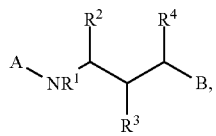

(XIV)

wherein A is selected from an aromatic ring, a heterocycle, a fused ring system, and a multiple ring system; wherein B is selected from an aromatic ring and a heterocycle; and wherein $R^2$, $R^3$ and $R^4$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; $R^1$ is selected from H, —CH$_3$, —CH$_2$CH$_3$, —CF$_3$; or a pharmaceutically acceptable salt thereof;

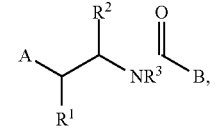

(XV)

wherein A is selected from an aromatic ring, a heterocycle, a fused ring system, and a multiple ring system; wherein B is selected from an aromatic ring and a heterocycle; and wherein $R^1$ and $R^2$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; $R^3$ is selected from H, —CH$_3$, —CH$_2$CH$_3$, —CF$_3$; or a pharmaceutically acceptable salt thereof; and

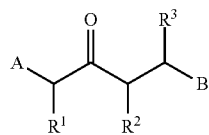

(XVI)

wherein A is selected from an aromatic ring, a heterocycle, a fused ring system, and a multiple ring system; wherein B is selected from an aromatic ring and a heterocycle; and wherein $R^1$, $R^2$, and $R^3$ are independently selected from H, —CH$_3$, —CH$_2$CH$_3$, —CH$_2$CH$_2$CH$_3$, —CH(CH$_3$)$_2$, —CF$_3$, —OH, —OCH$_3$, OCH$_2$CH$_3$, —NH$_2$, —N(CH$_3$)$_2$, —N(CH$_3$)$_3$, and —N(CH$_2$CH$_3$)$_2$; or a pharmaceutically acceptable salt thereof.

Particularly suitable GPR183 antagonists are selected from:

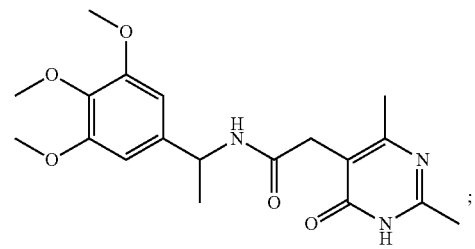

(SAE-1)

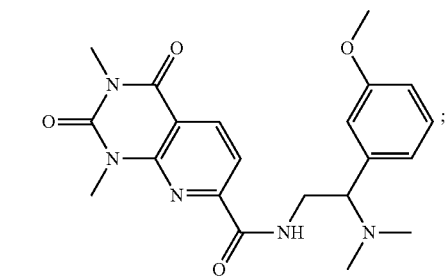

(SAE-4)

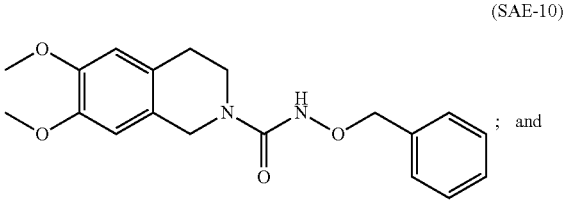

(SAE-10)

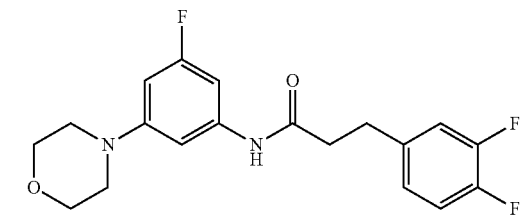

(SAE-14)

or pharmaceutically acceptable salts thereof.

In one aspect, the GPR183 antagonist is a compound of Formula (XVI), or a pharmaceutically acceptable salt thereof;

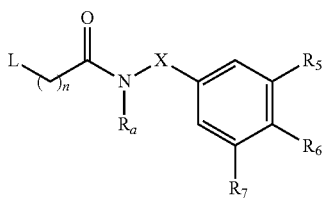

Formula (XVII)

wherein:
X is alkyl comprising 5 or fewer carbons optionally with one or more carbons replaced with one or more of oxygen and nitrogen, or X is a bond;
$R_5$, $R_6$, and $R_7$ are independently selected from hydrogen, halo, alkyl, alkoxy, haloalkyl, $N(R_b)(R_c)$, substituted or unsubstituted heterocyclo, or $R_5$ and $R_6$ or $R_6$ and $R_7$ together with the atoms they are attached to form a substituted or unsubstituted fused ring system;
$R_b$ and $R_c$ are independently hydrogen or alkyl;
$R_a$ is H alkyl, or $R_a$ forms a fused ring system with L or with the phenyl group connected to X;
n is 0-5;
L is substituted or unsubstituted aryl, substituted or unsubstituted heteroaryl, substituted or unsubstituted heterocyclo, or a substituted or unsubstituted fused ring system.

In various embodiments, n is 0 such that there is a bond between L and the carbonyl carbon of the amide. In other embodiments, n is 1-5 such that there is an alkyl linking group between L and the carbonyl carbon of the amide.

In various embodiments, X is a bond between the nitrogen of the amide and the phenyl group attached to X. In other embodiments, X is a linking group between the nitrogen of the amide and the phenyl group attached to X. In some embodiments, X is alkyl, —O-alkyl, alkyl-O-alkyl, alkyl-O—, or alkyl substituted with an amine wherein the amine may be H or alkyl substituted. In certain embodiments, X is —CH(CH$_3$)—, —CH$_2$CH(N(CH$_3$)$_2$)—, or —OCH$_2$—.

In various embodiments, L is a substituted or unsubstituted nitrogen containing ring system comprising one or two optionally aromatic rings and one or more carbonyl groups. In some embodiments, L comprises a pyrimidine derivative.

In various embodiments. $R_a$ forms a fused ring system with L or with the phenyl group connected to X. For example, in some embodiments $R_a$ comprises sufficient carbon, hydrogen, oxygen, and nitrogen atoms to form a cyclic, heterocyclic, aryl, or heteroaryl ring interlocked with L and/or the phenyl group connected to X. In some embodiments, this fused ring system provides additional stability or rigidity to the molecule which predisposes the compound to a favorable conformation for binding with a binding site in GPR183. In some embodiments, $R_a$ is alkyl. In other embodiments, $R_a$ is hydrogen.

In various embodiments, one or more of $R_5$, $R_6$, and $R_7$ are methoxy or ethoxy.

In various embodiments, L is

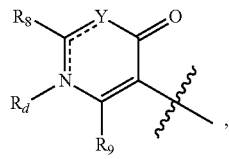

wherein:
the dashed lines represent a double bond on either N or Y,
Y is $CR_{10}R_{11}$ or N—$R_e$ when the double bond is on N or is $CR_{12}$ or nitrogen when the double bond in on Y;
$R_e$ is hydrogen or alkyl;
$R_d$ is H or alkyl when the double bond is on Y or is absent when the double bond is on N; and
$R_8$, $R_9$, $R_{10}$, $R_{11}$, and $R_{12}$ are independently hydrogen, alkyl, or alkoxy.

Various provisos may apply to the compounds of Formula (XVII) and pharmaceutically acceptable salts thereof when L is

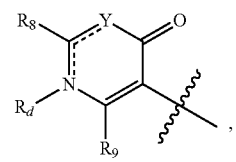

For example, in some embodiments, Y is N—$R_e$ when the double bond is on N. In some embodiments, Y is nitrogen when the double bond in on Y. In certain embodiments, the double bond is on N, Y is N—$R_e$, and $R_d$ is absent.

Additionally or alternatively, when L is

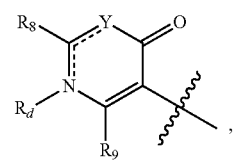

in some embodiments $R_8$ and $R_9$ are alkyl. In certain embodiments $R_8$ and $R_9$ are methyl or ethyl.

Additionally or alternatively, when L is

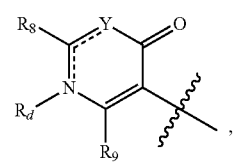

in some embodiments n is 1 or 2.

Additionally or alternatively, when L is

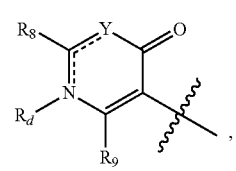

in some embodiments X is alkyl. In certain embodiments, X is —CH(CH$_3$)—.

Additionally or alternatively, when L is

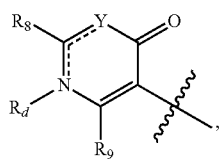

in some embodiments $R_5$, $R_6$, and $R_7$ are methoxy.

These provisos may be applied in combination. For example, for certain compounds of Formula (XVII) when L is

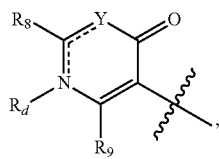

the double bond is on N, Y is N—$R_e$, and $R_d$ is absent; $R_8$ and $R_9$ are methyl; n is 1; X is —CH(CH$_3$)—; $R_5$, $R_6$, and $R_7$ are methoxy; and $R_a$ is H.

In one aspect, the GPR183 antagonist is a compound of Formula (XVIII), or a pharmaceutically acceptable salt thereof Formula (XVIII)

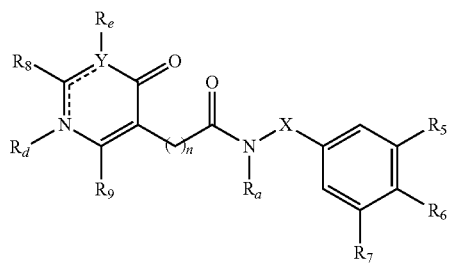

wherein:
- X is alkyl comprising 5 or fewer carbons optionally with one or more carbons replaced with one or more of oxygen and nitrogen, or X is a bond;
- $R_5$, $R_6$, and $R_7$ are independently selected from hydrogen, halo, alkyl, alkoxy, haloalkyl, N($R_b$)($R_c$), substituted or unsubstituted heterocyclo, or $R_5$ and $R_6$ or $R_6$ and $R_7$ together with the atoms they are attached to form a substituted or unsubstituted fused ring system;
- $R_b$ and $R_c$ are independently hydrogen or alkyl;
- $R_a$ is H, alkyl, or $R_a$ forms a fused ring system with A or with the phenyl group connected to X;
- n is 0-5;
- the dashed lines represent a double bond on either N or Y; and
- Y is CR$_{10}$R$_{11}$ or N—$R_e$ when the double bond is on N or is CR$_{12}$ or N when the double bond in on Y.

Various provisos may apply to the compounds of Formula (XVIII) and pharmaceutically acceptable salts thereof. For example, in some embodiments, Y is N—$R_e$ when the double bond is on N or is nitrogen when the double bond in on Y. In some embodiments, the double bond is on N, Y is N—$R_e$, and $R_d$ is absent.

Additionally or alternatively, in some embodiments of compounds of Formula (XVIII), n is 1 or 2.

Additionally or alternatively, in some embodiments of compounds of Formula (XVIII), X is alkyl or —O-alkyl. In certain embodiments, X is —CH(CH$_3$)—, —CH$_2$CH(N(CH$_3$)$_2$)—, or —OCH$_2$—.

Additionally or alternatively, in some embodiments of compounds of Formula (XVIII), $R_8$ and $R_9$ are methyl or ethyl.

These provisos may be applied in combination. For example, for certain compounds of Formula (XVIII), the double bond is on N; Y is N—$R_e$; $R_d$ is absent; $R_8$ and $R_9$ are methyl; n is 1; X is —CH(CH$_3$)—; $R_5$, $R_6$, and $R_7$ are methoxy; and $R_a$ is H.

In various embodiments, L is

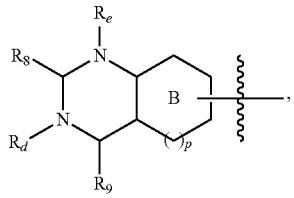

wherein:
- p is 0-3 such that ring B is a 5-8 membered, substituted or unsubstituted, aryl, heteroaryl, alkyl, or heterocylic ring;
- $R_8$ and $R_9$ are independently hydrogen, alkyl, alkoxy, —OH, or together with the atoms they are attached to form a carbonyl group; and
- $R_d$ and $R_e$ are independently H or alkyl.

Various provisos may apply to the compounds of Formula (XVII) and pharmaceutically acceptable salts thereof when L is

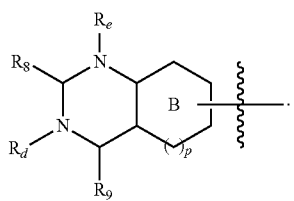

For example, in some embodiments, p is 1 and ring B is aryl or heteroaryl. In some embodiments, ring B is pyridine.

Additionally or alternatively, when L is

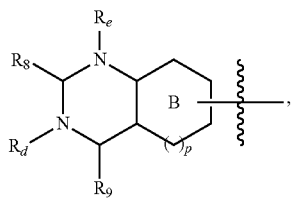

in some embodiments, ring B is connected to the rest of L by a shared bond at the 5,6 position and is connected to the rest for Formula (I) at the 2 position respective the nitrogen on the pyridine.

Additionally or alternatively, when L is

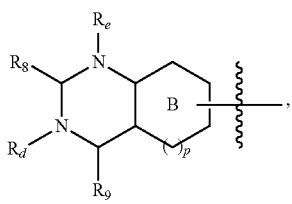

in some embodiments, $R_8$ and $R_9$ are independently alkoxy, —OH, or together with the atoms they are attached to form carbonyl group. In some embodiments, $R_8$ and $R_9$ together with the atoms they are attached to form carbonyl groups.

Additionally or alternatively, when L is

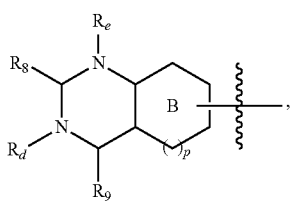

in some embodiments $R_e$ and $R_d$ are alkyl. In certain embodiments, $R_e$ and $R_d$ are methyl or ethyl.

Additionally or alternatively, when L is

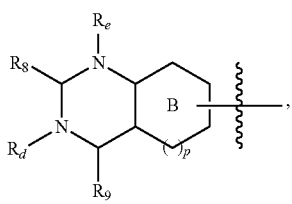

in some embodiments, n is 0.

Additionally or alternatively, when L is

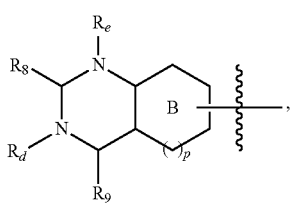

in some embodiments, X is alkyl comprising 5 or fewer carbons with one or more carbons replaced with a nitrogen. In certain embodiments, X is —CH$_2$CH(N(CH$_3$)$_2$)—.

Additionally or alternatively, when L is

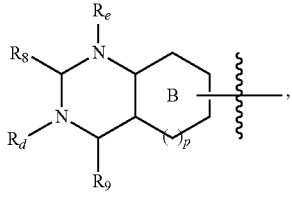

in some embodiments, $R_5$ is methoxy and $R_6$ and $R_7$ are H.

These provisos may be applied in combination. For example, for certain compounds of Formula (XVII) when L is

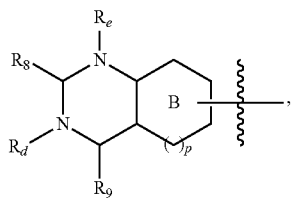

p is 1; ring B is pyridine; ring B is connected to the rest of A by a shared bond at the 5,6 position and is connected to the rest for Formula (XVII) at the 2 position respective the nitrogen on the pyridine; $R_8$ and $R_9$ together with the atoms they are attached to form a carbonyl group; $R_e$ and $R_d$ are methyl; n is 0; X is —CH$_2$CH(N(CH$_3$)$_2$)—; $R_5$ is methoxy; $R_6$ and $R_7$ are H; and $R_a$ is H.

In one aspect, the GPR183 antagonist is a compound of Formula (XIX), or a pharmaceutically acceptable salt thereof,

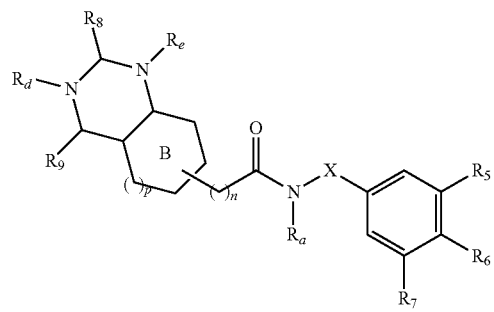

Formula (XIX)

wherein:
X is alkyl comprising 5 or fewer carbons optionally with one or more carbons replaced with one or more of oxygen and nitrogen, or X is a bond;
$R_5$, $R_6$, and $R_7$ are independently selected from hydrogen, halo, alkyl, alkoxy, haloalkyl, N($R_b$)($R_c$), substituted or unsubstituted heterocyclo, or $R_5$ and $R_6$ or $R_6$ and $R_7$ together with the atoms they are attached to form a substituted or unsubstituted fused ring system;
$R_b$ and $R_c$ are independently hydrogen or alkyl;
$R_a$ is H, alkyl, or $R_a$ forms a fused ring system with A or with the phenyl group connected to X;
n is 0-5;
p is 0-3 such that ring B is a 5-8 membered, substituted or unsubstituted, aryl, heteroaryl, alkyl, or heterocylic ring;
$R_8$ and $R_9$ are independently hydrogen, alkyl, alkoxy, —OH, or together with the atoms they are attached to form a carbonyl group; and
$R_d$ and $R_e$ are independently H or alkyl.

Various provisos may apply to the compounds of Formula (XIX) and pharmaceutically acceptable salts thereof. For example, in some embodiments, p is 1 and ring B is aryl or heteroaryl. In certain embodiments, ring B is pyridine.

In some embodiments of compounds of Formula (XIX), the compound has a structure consisting of

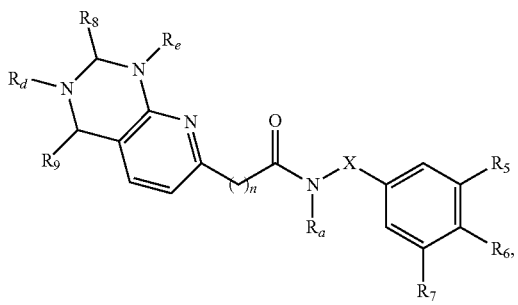

wherein $R_5$, $R_6$, $R_7$, $R_8$, $R_9$, $R_a$, $R_e$, $R_d$, n, and X are as defined above.

Additionally or alternatively, in some embodiments of compounds of Formula (XIX), $R_8$ and $R_9$ are independently alkoxy, —OH, or together with the atoms they are attached to form a carbonyl group. In some embodiments, $R_8$ and $R_9$ together with the atoms they are attached to form a carbonyl group.

Additionally or alternatively, in some embodiments of compounds of Formula (XIX), $R_e$ and $R_d$ are alkyl. In certain embodiments, $R_e$ and $R_d$ are methyl or ethyl.

Additionally or alternatively, in some embodiments of compounds of Formula (XIX), n is 0.

Additionally or alternatively, in some embodiments of compounds of Formula (XIX), X is alkyl comprising 5 or fewer carbons with one or more carbons replaced with a nitrogen. In certain embodiments, X is —CH$_2$CH(N(CH$_3$)$_2$)—.

Additionally or alternatively, in some embodiments of compounds of Formula (XIX), one of $R_5$, $R_6$, and $R_7$ is methoxy or ethoxy. In certain embodiments, one of $R_5$, $R_6$, and $R_7$ is methoxy or ethoxy and two of $R_5$, $R_6$, and $R_7$ are H.

These provisos may be applied in combination. For example, for certain compounds of Formula (XIX), the compound has a structure consisting of

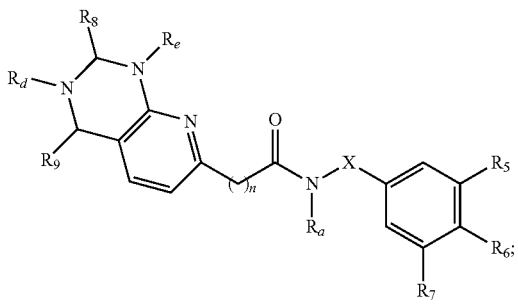

$R_8$ and $R_9$ together with the atoms they are attached to form a carbonyl group; $R_e$ and $R_d$ are methyl; n is 0; X is —CH$_2$CH(N(CH$_3$)$_2$)—; $R_5$ is methoxy; $R_6$ and $R_7$ are H; and $R_a$ is H.

In various embodiments, for the compound of Formula XVIII, L is a substituted or unsubstituted nitrogen containing ring system comprising one or two optionally aromatic rings and one or more alkoxy substituents. In certain embodiments, the ring system comprises at least one aromatic ring.

In various embodiments, for the compound of Formula (XVIII), L is

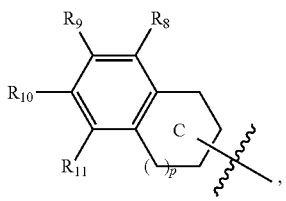

wherein:
p is 0-3 such that C is a 5-8 membered, substituted or unsubstituted, heteroaryl or heterocyclo ring comprising one or more nitrogens; and
$R_8$, $R_9$, $R_{10}$, and $R_{11}$ are independently hydrogen, alkyl, alkoxy, or —OH.

Various provisos may apply to the compounds of Formula (XVI) and pharmaceutically acceptable salts thereof when L is

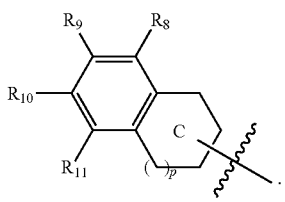

For example, in some embodiments, p is 1 such that ring C is a 6 membered ring. In some embodiments, ring C is heterocyclo. In certain embodiments, ring C is 3-piperidine.

Additionally or alternatively, in some embodiments when L is

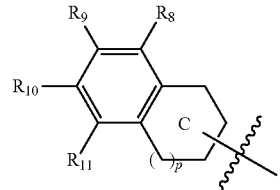

L is connected to the rest of Formula (I) by a bond with a nitrogen in ring C.

Additionally or alternatively, in some embodiments when L is

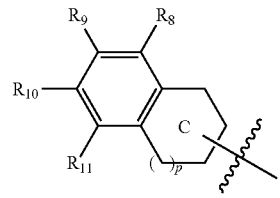

at least one of $R_8$, $R_9$, $R_{10}$, and $R_{11}$ is alkoxy or —OH. In some embodiments, $R_8$ and $R_{11}$ are H and $R_9$ and $R_{10}$ are methoxy or ethoxy.

Additionally or alternatively, in some embodiments when L is

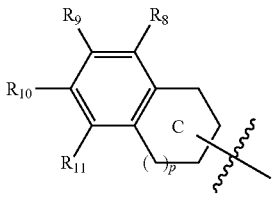

X is alkyl comprising 5 or fewer carbons with one or more carbons replaced with an oxygen. In some embodiments, X is —OCH$_2$—

Additionally or alternatively, in some embodiments when L is

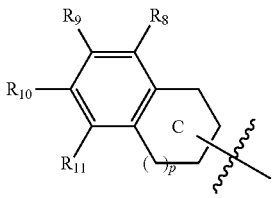

n is 0.

Additionally or alternatively, in some embodiments when L is

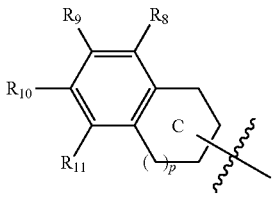

$R_5$, $R_6$, and $R_7$ are H.

These provisos may be applied in combination. For example, for certain compounds of Formula (XVII) when L is

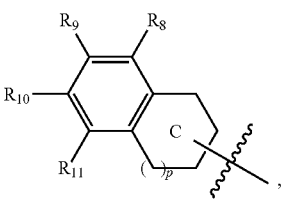

p is 1; ring C is 3-piperidine; A is connected to the rest of Formula (XVII) by a bond with a nitrogen in ring C; $R_8$ and $R_{11}$ are H and $R_9$ and $R_{10}$ are methoxy; n is 0; X is —OCH$_2$—; $R_5$, $R_6$, and $R_7$ are H; and $R_a$ is H.

In one aspect, the GPR183 antagonist is a compound of Formula (XX), or a pharmaceutically acceptable salt thereof,

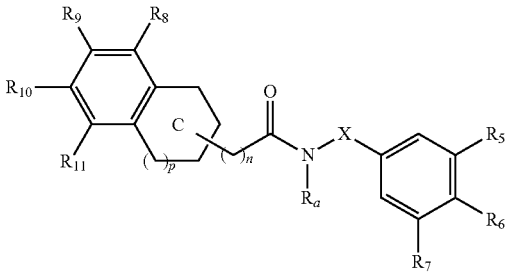

Formula (XX)

Wherein:
X is alkyl comprising 5 or fewer carbons optionally with one or more carbons replaced with one or more of oxygen and nitrogen, or X is a bond;
$R_5$, $R_6$, and $R_7$ are independently selected from hydrogen, halo, alkyl, alkoxy, haloalkyl, N($R_b$)($R_c$), substituted or unsubstituted heterocyclo, or $R_5$ and $R_6$ or $R_6$ and $R_7$ together with the atoms they are attached to form a substituted or unsubstituted fused ring system;
$R_b$ and $R_c$ are independently hydrogen or alkyl;
$R_a$ is H, alkyl, or $R_a$ forms a fused ring system with ring C or with the phenyl group connected to X;
n is 0-5;
p is 0-3 such that C is a 5-8 membered, substituted or unsubstituted, heteroaryl or heterocyclo ring comprising one or more nitrogens; and
$R_8$, $R_9$, $R_{10}$, and $R_{11}$ are independently hydrogen, halo, alkyl, alkoxy, or —OH.

Various provisos may apply to the compounds of Formula (XX) and pharmaceutically acceptable salts thereof. For example, in some embodiments, p is 1 such that ring C is a 6 membered ring. In some embodiments, ring C is heterocyclo. In certain embodiments, ring C is 3-piperidine.

Additionally or alternatively, in some embodiments of compounds of Formula (XX), ring C is connected to the rest of Formula (XX) by a bond with a nitrogen in ring C.

Additionally or alternatively, in some embodiments of compounds of Formula (XX), at least one of $R_8$, $R_9$, $R_{10}$, and $R_{11}$ is alkoxy or —OH. In certain embodiments, $R_8$ and $R_{11}$ are H and $R_9$ and $R_{10}$ are alkoxy. In certain embodiments, $R_8$ and $R_{11}$ are H and $R_9$ and $R_{10}$ are methoxy or ethoxy.

Additionally or alternatively, in some embodiments of compounds of Formula (XX), X is alkyl comprising 5 or fewer carbons with one or more carbons replaced with an oxygen. In certain embodiments, X is —OCH$_2$—

Additionally or alternatively, in some embodiments of compounds of Formula (XX), n is 0.

Additionally or alternatively, in some embodiments of compounds of Formula (XX), $R_5$, $R_6$, and $R_7$ are H.

These provisos may be applied in combination. For example, for certain compounds of Formula (XX), p is 1; ring C is 3-piperidine; ring C is connected to the rest of Formula (XX) by a bond with a nitrogen in ring C; $R_8$ and $R_{11}$ are H and $R_9$ and $R_{10}$ are methoxy; n is 0; X is —OCH$_2$—; $R_5$, $R_6$, and $R_7$ are H; and $R_a$ is H.

In various embodiments, for the compound of Formula (XVII), L is substituted monocyclic aryl or substituted monocyclic heteroaryl.

In various embodiments, for the compound of Formula (XVII), L is

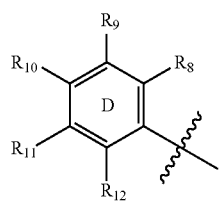

wherein:
ring D is a 6-membered aromatic ring optionally comprising 1 or more nitrogens;
and
$R_8$, $R_9$, $R_{10}$, $R_{11}$, and $R_{12}$ are independently hydrogen, halo, alkyl, alkoxy, or —OH.

Various provisos may apply to the compounds of Formula (XVII) and pharmaceutically acceptable salts thereof when L

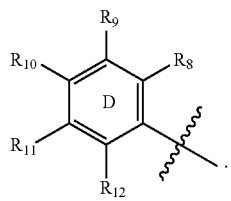

For example, in some embodiments, ring D is aryl.

Additionally or alternatively, when L is

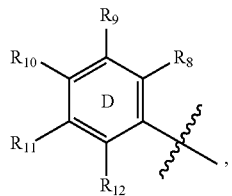

in some embodiments at least one of $R_8$, $R_9$, $R_{10}$, $R_{11}$, and $R_{12}$ is halo. In certain embodiments, $R_9$ and $R_{10}$ are halo and $R_8$, $R_{11}$, and $R_{12}$ are hydrogen. In certain embodiments, $R_9$ and $R_{10}$ are F and $R_8$, $R_{11}$, and $R_{12}$ are hydrogen.

Additionally or alternatively, when L is

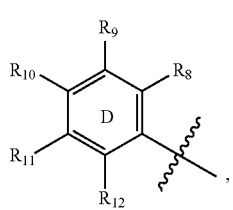

in some embodiments n is 1-3. In certain embodiments, n is 2.

Additionally or alternatively, when L is

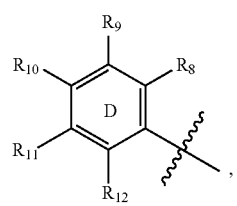

in some embodiments X is a bond.

Additionally or alternatively, when L is

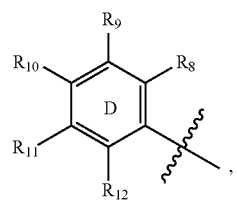

in some embodiments at least one of $R_5$, $R_6$, and $R_7$ is halo. In certain embodiments, $R_5$ is F.

Additionally or alternatively, when L is

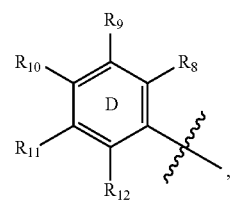

in some embodiments at least one of $R_5$, $R_6$, and $R_7$ is heterocyclo. In certain embodiments, $R_7$ is morpholinyl. In certain embodiment, the morpholinyl is bonded to Formula (XVII) by the nitrogen of the morpholinyl.

These provisos may be applied in combination. For example, for certain compounds of Formula (XVII) when L is

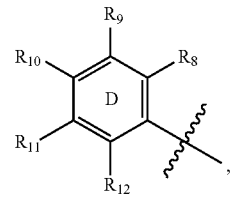

ring D is a 6-membered aryl ring; $R_9$ and $R_{10}$ are F; $R_8$, $R_{11}$ and $R_{12}$ are hydrogen; n is 2; X is a bond; $R_5$ is F; $R_6$ is H; $R_7$ is morpholinyl; and $R_a$ is H.

In one aspect, the GPR183 antagonist is a compound of Formula (XXI), or a pharmaceutically acceptable salt thereof, Formula (XXI)

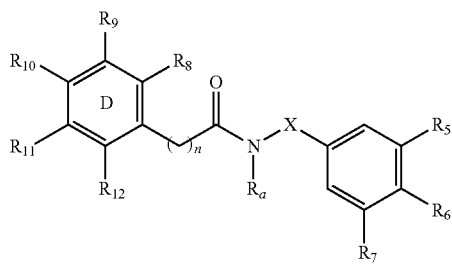

wherein:
- X is alkyl comprising 5 or fewer carbons optionally with one or more carbons replaced with one or more of oxygen and nitrogen, or X is a bond;
- $R_5$, $R_6$, and $R_7$ are independently selected from hydrogen, halo, alkyl, alkoxy, haloalkyl, $N(R_b)(R_c)$, substituted or unsubstituted heterocyclo, or $R_5$ and $R_6$ or $R_6$ and $R_7$ together with the atoms they are attached to form a substituted or unsubstituted fused ring system;
- $R_b$ and $R_c$ are independently hydrogen or alkyl;
- $R_a$ is H, alkyl, or $R_a$ forms a fused ring system with D or with the phenyl group connected to X;
- n is 0-5; and
- ring D is a 6-membered aromatic ring optionally comprising 1 or more nitrogens, and $R_8$, $R_9$, $R_{10}$, $R_{11}$, and $R_{12}$ are independently hydrogen, halo, alkyl, alkoxy, or —OH.

Various provisos may apply to the compounds of Formula (XXI) and pharmaceutically acceptable salts thereof. For example, in some embodiments, ring D is aryl.

Additionally or alternatively, in some embodiments of compounds of Formula (XXI), at least one of $R_8$, $R_9$, $R_{10}$, $R_{11}$, and $R_{12}$ is halo. In certain embodiments, $R_9$ and $R_{10}$ are halo and $R_8$, $R_{11}$, and $R_{12}$ are hydrogen. In certain embodiments, $R_9$ and $R_{10}$ are F and $R_8$, $R_{11}$, and $R_{12}$ are hydrogen.

Additionally or alternatively, in some embodiments of compounds of Formula (XXI), n is 1-3. In certain embodiments, n is 2.

Additionally or alternatively, in some embodiments of compounds of Formula (XXI), X is a bond.

Additionally or alternatively, in some embodiments of compounds of Formula (XXI), at least one of $R_5$, $R_6$, and $R_7$ is halo. In certain embodiments, $R_5$ is F.

Additionally or alternatively, in some embodiments of compounds of Formula (XXI), at least one of $R_5$, $R_6$, and $R_7$ is heterocyclo. In certain embodiments, $R_7$ is morpholinyl. In certain embodiments, the morpholinyl is bonded to Formula (XXI) at the nitrogen of the morpholinyl.

These provisos may be applied in combination. For example, for certain compounds of Formula (XXI), ring D is a 6-membered aryl ring; $R_9$ and $R_{10}$ are F; $R_8$, $R_{11}$, and $R_{12}$ are hydrogen; n is 2; X is a bond; $R_5$ is F; $R_6$ is H; $R_7$ is morpholinyl; and $R_a$ is H.

In some embodiments, the compound of Formula (XVII) can be:

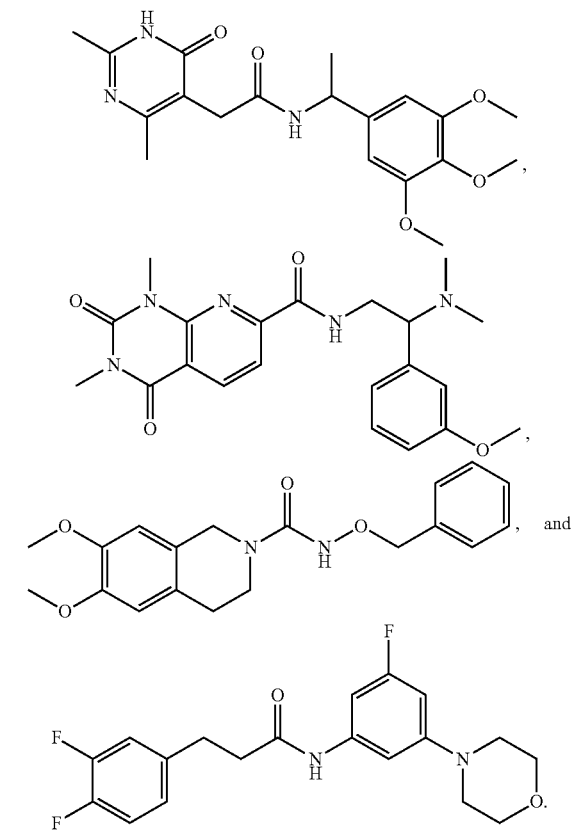

The term "alkoxy," as used herein, refers to an alkyl group, as defined herein, appended to the parent molecular moiety through an oxygen atom.

The term "alkyl", as used herein, refers to a straight- or branched-chain alkyl group having from 1 to about 20 carbon atoms in the chain. For example, the alkyl group can be a $(C_1-C_{20})$alkyl, a $(C_1-C_{12})$alkyl, $(C_1-C_8)$alkyl, $(C_1-C_6)$alkyl, or $(C_1-C_4)$alkyl. Examples of alkyl groups include methyl (Me), ethyl (Et), n-propyl, isopropyl, butyl, isobutyl, sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples. Alkyl groups can be optionally substituted or unsubstituted.

The term "aryl", as used herein, refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-14 carbon atoms, about 6-13 carbon atoms, or about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "cycloalkyl", as used herein, refers to a saturated or partially saturated, monocyclic, fused polycyclic, or spiro polycyclic carbocycle having from 3 to 12 ring atoms per carbocycle, and can be optionally substituted or unsubstituted. In some embodiments, an alkyl group refers to a cycloalkyl group that accordingly includes a ring structure. Such alkyl groups include (cycloalkyl)-alkyl groups.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups can be unsubstituted or substituted by one or more suitable substituents, preferably 1 to 5 suitable substituents.

The term "heterocyclo," "heterocycle," or "heterocyclyl." as used herein, refers to a monocyclic, bicyclic, tricyclic, fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members, and can be optionally substituted or unsubstituted. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups can be unsubstituted or substituted by one or more suitable substituents, preferably 1 to 3 suitable substituents, as defined above.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}O$, $^{17}O$, $^{31}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. When referring to any formula given herein, the selection of a particular moiety from a list of possible species for a specified variable is not intended to limit the definition of the moiety for the variable appearing elsewhere. In other words, where a variable appears more than once, the choice of the species from a specified list is independent of the choice of the species for the same variable elsewhere in the formula, or elsewhere in a different formula.

As to any of the groups or "substituents" described herein, each can further include one or more (e.g., 1, 2, 3, 4, 5, or 6) substituents. It is understood, of course, that such groups do not contain any substitution or substitution patterns which are sterically impractical and/or synthetically non-feasible.

The term "substituted" means that a specified group or moiety can bear one or more (e.g., 1, 2, 3, 4, 5, or 6) substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted in some embodiments but can be substituted in other embodiments.

Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and/or cyano. In certain embodiments, any one of the above groups can be included or excluded from a variable or from a group of substituents.

Selected substituents within the compounds described herein may be present to a recursive degree. In this context. "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. In some embodiments, the substitution will result in a compound having a molecular weight of less than about 1200 Da, less than about 1000 Da, less than about 900 Da, less than about 800 Da, less than about 750 Da, less than about 700 Da, less than about 650 Da, less than about 600

Da, less than about 500 Da, or less than about 400 Da. Recursive substituents are an intended aspect of the invention. One of ordinary skill in the art of medicinal and organic chemistry understands the versatility of such substituents.

Other suitable GPR183 antagonists include, for example, spirocyclic EBI2 modulators as disclosed in WO 2015048567, which is incorporated herein by reference in its entirety; amide derivatives of EBI2 modulators as disclosed in WO 2015048570, which is incorporated herein by reference in its entirety; modulators of the interaction between EB2 and hydroxycholesterols as disclosed in WO 2010066689, which is incorporated herein by reference in its entirety; NIBR189 as disclosed in Gessier et al. (J. Med. Chem., 2014, 57(8):3358-3368), which is incorporated herein by reference in its entirety; GSK682753 as disclosed in Benned-Jensen et al. (J. Biol. Chem., 2011, 286(33): 29292-29302), which is incorporated herein by reference in its entirety; fluro analogs of bioactive oxysterols as disclosed in Deng et al. (Bioorganic & Medicinal Chemistry Letters, 2016, 26(20:4888-4891), which is incorporated herein by reference in its entirety; and inhibitors of cytochrome P450 family 7 subfamily B member 1 (CYP7B1) as disclosed in WO 2018115319, which is incorporated herein by reference in its entirety.

Other suitable GPR183 antagonists include, for example, small inhibitory RNAs. Suitable siRNAs include, for example, GAAGCUUCGUUUCUCUAAU (SEQ ID NO:1), GCAGGAGGCUGAAAGGAUU (SEQ ID NO:2), GUCAGUGUAUCGAUUUCUA (SEQ ID NO:3), and combinations thereof, as disclosed in U.S. Pat. No. 8,497, 075, which is incorporated herein by reference in its entirety.

Other suitable GPR183 antagonists can be made and identified using the methods described in U.S. Pat. No. 8,497,075, which is incorporated herein by reference in its entirety.

Pain can be at least one of chemotherapy-induced neuropathy, diabetic neuropathy, cancer pain, autoimmune neuropathy, and traumatic neuropathy. As a prophylactic, the GPR183 can be administered to prevent pain associated with chemotherapy-induced neuropathy, diabetic neuropathy, cancer pain, autoimmune neuropathy, and traumatic neuropathy.

As used herein, "subject in need thereof" (also used interchangeably herein with "a patient in need thereof") refers to a subject susceptible to or at risk of a specified disease, disorder, or condition. The methods disclosed herein can be used with a subset of subjects who are susceptible to or at elevated risk for pain. Because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions. Formulations of the present disclosure can be administered to "a subject in need thereof". As used herein, "a subject" (also interchangeably referred to as "an individual" and "a patient") refers to animals including humans and non-human animals. Accordingly, the compositions and methods disclosed herein can be used for human and veterinarian applications, particularly human and veterinarian medical applications. Suitable subjects include warm-blooded mammalian hosts, including humans, companion animals (e.g., dogs, cats), cows, horses, mice, rats, rabbits, primates, and pigs, preferably a human patient.

Suitable methods for administration of formulations of the present disclosure are by parenteral (e.g., intravenous (IV), intramuscular (IM), subcutaneous (SC), or intraperitoneal (IP)) routes and the formulations administered ordinarily include effective amounts of product in combination with acceptable diluents, carriers and/or adjuvants. Standard diluents such as human serum albumin are contemplated for pharmaceutical compositions of the disclosure, as are standard carriers as described herein.

Formulations for parenteral administration (e.g. by injection, for example bolus injection or continuous infusion) can be presented in unit dose form in ampoules, pre-filled syringes, small volume infusion or in multi-dose containers with and without an added preservative. The formulations can take such forms as suspensions, solutions, or emulsions in oily or aqueous vehicles, and may contain formulation agents such as suspending, stabilizing and/or dispersing agents.

As used herein, an "effective amount", a "therapeutically effective amount", a "prophylactically effective amount", and a "diagnostically effective amount" is the amount of the GPR183 antagonist needed to elicit the desired biological response following administration. The amount of the GPR183 antagonist will depend on the form of the GPR183 antagonist. Effective dosages are expected to vary substantially depending upon the GPR183 antagonist used and the specific disease, disorder, or condition treated.

Suitable dosage can be determined by one of skill in the art and can also be adjusted by the individual physician in the event of any complication. Typically, the dosage of a composition comprising a GPR183 antagonist can range from about 0.001 mg/kg body weight to about 5 g/kg body weight. In some embodiments, the dosage range ranges from about 0.001 mg/kg body weight to about 1 g/kg body weight, from about 0.001 mg/kg body weight to about 0.5 g/kg body weight, from about 0.001 mg/kg body weight to about 0.1 g/kg body weight, from about 0.001 mg/kg body weight to about 50 mg/kg body weight, from about 0.001 mg/kg body weight to about 25 mg/kg body weight, from about 0.001 mg/kg body weight to about 10 mg/kg body weight, from about 0.001 mg/kg body weight to about 5 mg/kg body weight, from about 0.001 mg/kg body weight to 1 about mg/kg body weight, from about 0.001 mg/kg body weight to about 0.1 mg/kg body weight, or from about 0.001 mg/kg body weight to about 0.005 mg/kg body weight. Alternatively, in some embodiments the dosage range is from 0.1 g/kg body weight to about 5 g/kg body weight, from about 0.5 g/kg body weight to about 5 g/kg body weight, from about 1 g/kg body weight to about 5 g/kg body weight, from about 1.5 g/kg body weight to about 5 g/kg body weight, from about 2 g/kg body weight to about 5 g/kg body weight, from about 2.5 g/kg body weight to about 5 g/kg body weight, from about 3 g/kg body weight to about 5 g/kg body weight, from about 3.5 g/kg body weight to about 5 g/kg body weight, from about 4 g/kg body weight to about 5 g/kg body weight, or from about 4.5 g/kg body weight to about 5 g/kg body weight. Suitable dosage for use in the methods of the present disclosure will depend upon a number of factors including, for example, age and weight of an individual, the specific disease, disorder, or condition treated, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

Suitable routes of administration include oral, sublingual, transdermal, subcutaneous, topical, absorption through epithelial or mucocutaneous linings, intravenous, intranasal, intraarterial, intramuscular, intratumoral, peritumoral, intraperitoneal, intrathecal, rectal, vaginal, or aerosol formulations. In some aspects, the pharmaceutical composition is administered orally or intravenously.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or (II) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

EXAMPLES

Example 1

Unbiased transcriptomic analyses of a model of traumatic nerve-injury induced neuropathic pain caused by constriction of the sciatic nerve in rats (CCI) revealed a significant increase in the G-protein coupled receptor. GPR183/EBI2 (Epstein-Barr virus-induced gene 2), within the dorsal horn of the spinal cord (DH-SC) ipsilateral to nerve injury. The primary endogenous ligand for GPR183 is the oxysterol, 7α,25-dihydroxycholesterol (7α,25-OHC). 7α,25-OHC induced a very prominent calcium response in HL-60 cells that express GPR183 (FIG. 1: See Table 1).

TABLE 1

| log(agonist) vs. normalized response - Variable slope | |
|---|---|
| Best-fit values | |
| LogEC50 | −7.372 |
| HillSlope | 0.8624 |
| EC50 | 4.244e−008 |
| Std. Error | |
| LogEC50 | 0.1117 |
| HillSlope | 0.1714 |
| 95% CI (profile likelihood) | |
| LogEC50 | −7.598 to −7.147 |
| HillSlope | 0.5926 to 1.319 |
| EC50 | 2.521e−008 to 7.121e−008 |
| Goodness of Fit | |
| Degrees of Freedom | 58 |
| R square | 0.7728 |

TABLE 1-continued

| log(agonist) vs. normalized response - Variable slope | |
|---|---|
| Absolute Sum of Squares | 26615 |
| Sy.x | 21.42 |
| Number of points | |
| # of X values | 66 |
| # Y values analyzed | 60 |

Using an in silico approach, a library of 5.5 million compounds was screened for similarity to a GPR183 pharmacophore model and then compounds with the highest similarity scores were docked and ranked based upon their thermodynamics of binding. The top 16 commercially available compounds were purchased and then tested for GPR183-specific agonism and antagonism in a calcium mobilization (FLIPR) assay. Four compounds were able to antagonize 7α,25-OHC-induced calcium mobilization with $IC_{50}$ values below 50 nM in a GPR183-specific manner (FIGS. 2-5). Data in rodents demonstrated that intrathecal (i.th.) injections of these GPR183 antagonists (i.e., SAE-14; $IC_{50}$=28.5 nM) at time of peak neuropathic pain (mechano/cold-allodynia) reversed allodynia in a time-dependent manner with no observable adverse side effects (FIGS. 6A-8B). These results unravel a functional role for GPR183 in the maintenance of neuropathic pain and identify GPR183 as a potential target for therapeutic intervention. Moreover, i.th. injections of 7α,25-OHC in rodents induced a dose and time-dependent mechano-allodynia ($ED_{50}$=0.031 ng; 95% CI:8×10$^5$-13; n=6/dose; 3 doses). Similar results were obtained with small molecule GPR183 agonist, (SLU-PP1492) confirming that direct activation of GPR183 can recapitulate behavioral phenotypes of neuropathic pain (i.e. allodynia). These effects were blocked by i.th. delivery of SAE-14 supporting GPR183 dependence as a mode of action. Similar results were obtained in male and female rodents. All studies were performed in blinded fashion.

The results presented herein demonstrate drug discovery efforts led to the identification of several small-molecule selective GPR183 antagonists with $IC_{50}$ values in the nM range. The compounds and methods disclosed herein provide new treatment modalities for pain associated with cancer, cancer treatment, or other types of neuropathic pain. These modalities can be used as an adjuvant to improve current therapies or as a high-performance replacement to current therapies. The compounds and methods can also provide new research tools, including agonists and antagonists for the study of the physiological relevance of GPR183 biology in general in health and disease.

Example 2

In this Example, several GPR183 antagonists were identified and demonstrates that GPR183 signaling in the spinal cord was pro-nociceptive.

Experimental Animals

Male and female ICR mice (8-9 weeks old; 25-40 g starting weight) or Sprague Dawley rats (8-9 weeks old; 250 g starting weight) from Envigo-Harlan Laboratories (Indianapolis, IN) were housed two to four per cage (rats) or five to ten per cage (mice) in a controlled environment (12 hour light/dark cycle) with food and water available ad libitum. All experiments were performed with experimenters blinded to treatment conditions. All experiments were performed in accordance with the guidelines of the International Association for the Study of Pain and the National Institutes of Health and approvals from the Saint Louis University Animal Care and Use Committee. Experiments were performed in both male and female rodents; similar results were obtained in both sexes, so data was combined.

Test Compounds

α,25-dihydroxycholesterol (7α,25-OHC) was purchased from Avanti Polar Lipids (Alabaster, AL) and dissolved in DMSO as a 2 mM stock. For injections 7α,25-OHC was diluted in saline. NIBR189 was purchased from Tocris Bioscience (Minneapolis, MN) and dissolved in DMSO as a 23 mM stock. For intrathecal injections, NIBR189 was diluted in saline. Fluoronated 7α,25-OHC analog (SLUPP-1492) was synthesized as described previously (Deng et al., 2016) (detailed methods below and continued in Supplemental methods) and prepared as a 10 mM stock in DMSO. For injections SLUPP-1492 was diluted in saline. SAE compounds were purchased from Enamine (Monmouth Jct., NJ), all compounds were purified via normal phase chromatography and had purities of ≥95%. 100 mM Stock solutions of the SAE compounds were prepared in DMSO. For intrathecal injections, SAE compounds were diluted in saline. Acute intrathecal (i.th.) injections of compounds were performed as described previously (Lu and Schmidtko, 2013), all compounds were administered intrathecally in a total volume of 5-10 μL.

Chronic Constriction Injury (CCI) Model

CCI of the left sciatic nerve of mice and rats was performed under general anesthesia as previously described (Yosten et al., 2020). Briefly, animals were anesthetized with 2% isoflurane/O2, the left thigh was shaved and disinfected with Dermachlor solution. A small incision (1-1.5 cm) was made in the middle of the lateral aspect of the left thigh to expose the sciatic nerve. The nerve was loosely ligated around the diameter at 3 distinct sites (1 mm apart) using silk sutures (6.0, mice; 4.0, rats). The surgical site was closed with a skin clip and disinfected and treated with topical lidocaine (2%). Sham animals underwent the same procedure without nerve ligation. Peak allodynia developed by D7-D10 following CCI surgery.

Behavioral Testing

Mechano-allodynia was measured as previously described (Yosten et al., 2020) using calibrated von Frey filaments (Stoelting; range in mice: 0.07-2.00 g; in rats: 2-26 g) using the Dixon up-and-down method (Dixon, 1991). Mechano-allodynia was defined as a significant (p<0.05) reduction in mechanical paw withdrawal threshold [PWT (g)] compared to baseline forces (before treatment).

Cold allodynia was measured as previously described using the acetone test (Xing et al., 2007; Yosten et al., 2020). Briefly, a small drop of acetone was applied to the hind paw of the animal using a flattened polyethylene tube and a syringe and the response to the cold stimulus was scored (0, no response; 1, brisk withdrawal or flick of the paw; 2. repeated flicking of the paw; 3. repeated flicking and licking of the paw). The test was repeated 3 times with an interval of 5 minutes between each application for each paw and the scores for each paw were summed and reported as the response score (maximum of 9). When mechanical and cold allodynia were measured on the same animal, mechano-allodynia was measured first with at least 15 minutes before testing cold allodynia.

Estrus Smears

Vaginal smears were taken for female mice and rats 5-7 days before experiment and after experiment until animals were sacrificed to confirm animals were cycling, and treatment did not alter their cycle. Cells were placed on a glass slide and allowed to dry, stained with Accustain (MilliporeSigma: Saint Louis, MO) for 45 seconds and rinsed, as previously described (Byers et al., 2012). Fixed cells were viewed under a light microscope to determine their stage of estrus cycle. All animals displayed normal estrus cycles.

RNA-Sequencing

On D10 after CCI, animals were perfused (1×PBS) under deep anesthesia and lower lumbar spinal cord was harvested and placed in RNA-Later. Total RNA was isolated using RNeasy Plus Universal Mini kit (Qaigen; Germantown, MD) according to manufacturer's protocols. RNA-Sequencing was performed in the Saint Louis University Genomics Core Facility, Total RNA samples were quality assessed using an Agilent Bioanalyzer RNA Nano chip and were determined to have an RNA integrity number of ≥9. Ribosomal RNA was depleted from total RNA using the Eukaryotic RiboMinus Core Module v2 (Life Technologies, Thermofisher) and libraries were constructed using the Ion Total RNA-seq v2 kit (Life Technologies, Thermofisher) according to the manufacturer's protocols. Sequencing was performed on an Ion Torrent Proton with a mean read length of ~140 nucleotides. Reads were aligned to the rat genome sequence (version rn6) using the TMAP (Torrent Mapping Program) aligner (Homer, 2011) map4 algorithm, requiring a minimum seed length of 20 nucleotides and allowing soft-clipping at both 5' and 3' ends to accommodate spliced reads. The nucleotide coverage for all non-redundant exons was calculated and normalized to total exon coverage using BEDTools (Quinlan and Hall, 2010) and custom scripts in R (Team, 2015). Expression values are given as total normalized nucleotide exon coverage per gene. Fold changes in gene expression and p values were calculated using R and Microsoft Excel.

RNASCOPE® n D10 after CCI surgery animals were perfused under deep anesthesia and with 4% paraformaldehyde and lower lumbar spinal cord was harvested and post-fixed in 4% paraformaldehyde. Spinal cord lumbar sections were cryo-sectioned at 10 micrometers and stained using the RNASCOPE® technique. Probes for rat Gfap (NM_017009.2, Probe-Rn-Gfap-C2), Aif1 (NM_017196.3, Probe-Rn-Aif1-C3), Rbfox3 (NM_001134498.2, Probe-Rn-Rbfox3-C2), and Gpr183 (NM_001109386.1, Probe-Rn-Gpr183) were incubated with tissue strictly according to the Manual RNA-SCOPE® Fluorescence Multiplex Protocol (v2) (Advanced Cell Diagnostics, Newark, CA). Sections were imaged as Z-stacks of the central lamina 1 and 2 region of the dorsal horn on a Lecia TCS SP8 confocal microscope using a 40× (NA 1.30) (Leica Microsystems. Buffalo Grove, IL). RNA-scope signal was dilated by 3 pixel diameters for large overview display purposes or else signal was dilated by 0.5 pixel diameters. For analysis, RNASCOPE® signal was dilated for each slice by 0.5 pixel diameters and Gpr183 was isolated by thresholding the channel on positive signal, setting a selection area, and applying it to the appropriate lineage marker (GFAP, Aif1, or Rbfox3) within FIJI (PMID 22743772) using a custom macro (Supplementary methods). Particle counts of the signals were made in the resulting overlapping region (which represented the major RNA pool of a particular cell) for each slice.

Oxysterol Quantification

Male Sprague Dawley rats underwent CCI surgery on D0 and were taken down on either D0, D5, or D11 after surgery. Rats were perfused under deep anesthesia with 1×PBS, ipsilateral dorsal horn spinal cord was harvested and flash-frozen in liquid nitrogen. Oxysterols were measured according to McDonald et. al. (2012).

An inactive homology model of GPR183 based largely upon the Chemokine Receptor CCR5 (5UIW) was downloaded from the GPCRdb. (Pándy-Szekeres et al., 2017) Using Schrödinger, protein preparation was run to minimize the energy of the protein (OPLS3 force field). Schrödinger Phase was then employed to build a pharmacophore hypothesis built around the binding of NIBR189 and GSK682753A in GPR183 using the automated build function within Phase for receptor-ligand complex pharmacophore. This included features such as: aromatic, hydrophobic, H-bond acceptor/donator, and size exclusion spheres. Using a freely available database from Enamine (Enamine_Diverse_REAL_druglike_5M library), 5 million compounds were screened for their "likeness" to the properties of the NIBR189 and GSK682753A separately. The top ten thousand screening hits from each screen based upon their feature matching with the two pharmacophores were chosen for further screening. The twenty thousand screening hits were then used in a high-throughput GLIDE docking and the top 800 compounds (4%) with the lowest GlideScores (computational estimate of binding) were chosen for more precise docking studies. The top 800 compounds (4%) with the lowest GlideScores were subjected to standard precision docking using flexible ligand sampling in GLIDE using the default settings. The compounds were then sorted based upon their predicted Log(S) values (all the compounds were pre-screened to have a Log(P) of less than 5). Compounds with Log(S) values larger than −4 were then sorted based upon their GlideScores and the top 16 commercially available compounds in that pool were then ordered from Enamine for initial in vitro screening.

Synthesis of SLUPP-1492

Material: The 25-hydroxycholesterol was purchased from ChemShuttle (Hayward. CA), all other reagents and solvents were purchased from Sigma-Aldrich (St. Louis, MO), Alfa Aesar (Ward Hill. MA), or J. T. Baker (Radnor, PA) and used as received.

The purities of the final compounds were characterized by high-performance liquid chromatography (HPLC) using a gradient elution program (Ascentis Express Peptide C18 column, acetonitrile/water 5/95→95/5, 5 min, 0.05% trifluoroacetic acid) and UV detection (245 nM). TLC was performed on Merck KGaA TLC silica gel 60 F254 plates. Visualization was accomplished by using phosphomolybdic acid solution followed by heat and by UV fluorescence (λmax 254 nm). 1H nuclear magnetic resonance (NMR) was obtained on a Bruker 400 MHz instrument and all chemical shifts are referenced to residual solvent peaks (details in supplemental methods).

Cell Line and Culture

The Human leukemia (HL)-60 cells (American Type Culture Collection; Manassas, VA) were cultivated in RPMI 1640 media containing 10% heat-inactivated fetal bovine serum (FBS), 1% penicillin, and 1% GlutaMax. Cells were passaged every 3 days and maintained at a cell concentration below $1 \times 10^6$ to prevent differentiation.

The cells were incubated at 37° C. under 5% $CO_2$.

Calcium Mobilization Assays

Serial dilutions (5×) of compounds were prepared in 50:1 HBSS/HEPES. HL-60 cells ($1 \times 10^7$) were incubated in 50:1 HBSS/HEPES containing 5 µM indo-1-AM (Thermo Fischer Scientific; Waltham. MA) and 0.05% pluronic acid for 0.5 hours at room temperature. Cells were centrifuged and washed with 50:1 HBSS/HEPES and resuspended in buffer. Cells were loaded onto a black 96-well Greiner Bio-One (Thermo Fischer Scientific; Waltham, MA) clear-bottom plate at 100,000 cells/well for a 5× dilution. For agonism assays, cells were immediately incubated for 15 minutes at 37° C. inside a FlexStation 3 Multimode Plate Reader (Molecular Devices; Sunnyvale, CA). Following the 15 minute incubation period, 5× of the compound was added and fluorescence was read for 150 seconds at 37° C. This method was utilized to determine the $EC_{80}$ value of 7α,25-OHC ($EC_{80}$=200 nM). For antagonism assays, before the addition of agonist, 5× of the antagonist was added and incubated for 15 minutes at 37° C. inside a FlexStation3. After allowing 15 minutes of equilibration, the determined $EC_{80}$ of 7α,25-OHC (200 nM) was added, and fluorescence was read for 150 secs at 37° C. Calcium mobilization was determined ratiometrically using $\lambda_{ex}$ 350 nm and $\lambda_{em}$ 405/490 nm. Dose-response data were normalized to a 0.5% DMSO vehicle control and the maximum response. From the normalized data, non-linear regression curves were then generated to calculate the appropriate $EC_{50}$ and $IC_{50}$ values. Each compound was run in triplicate (n=3).

siRNA Knock-Down of GPR183 siRNA was purchased from Santa Cruz Biotechnology (Dallas, TX). HL-60 cells were centrifuged and counted with a hemocytometer to obtain $2.5 \times 10^6$ cells. Transfection of the siRNA was performed with Lipofectamine 2000 reagent (Invitrogen; Calsbad, CA) and Opti-MEM. Lipofectamine and siRNA (200 pmol) were incubated at room temperature for 15 minutes before addition to 5 mL of cell suspension in media. Transfected cells were incubated at 37° C. under 5% $CO_2$ for 48 hours. HL-60 control cells were treated with Lipofectamine 2000 reagent without siRNA. After 48 hours cells were utilized in calcium mobilization assays.

Statistical Analysis

Data is expressed as mean SD or SEM for n biological replicates and analyzed by paired or unpaired t test or one-way or two-way repeated measures ANOVA with Dunnett's multiple comparisons. Sphericity was tested with Mauchly's test and Greenhouse-Geiser corrections were used when necessary. Significant differences were defined as $p<0.05$. Statistical analyses were performed using Graphpad Prism (versions 5.00-8.1.1, for Windows, GraphPad Software. San Diego, CA, www.graphpad.com).

Results

Figure 9A:
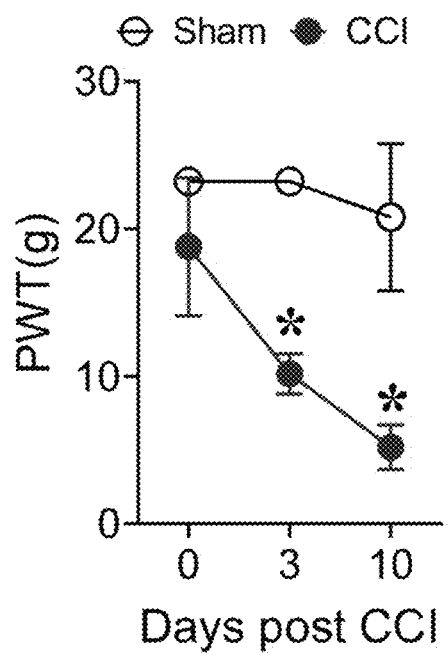
FIGS. 9A-9D depict the upregulation of Gpr183 expression in ipsilateral DH-SC from rats with CCI-induced neuropathic pain.
Figure 9B:
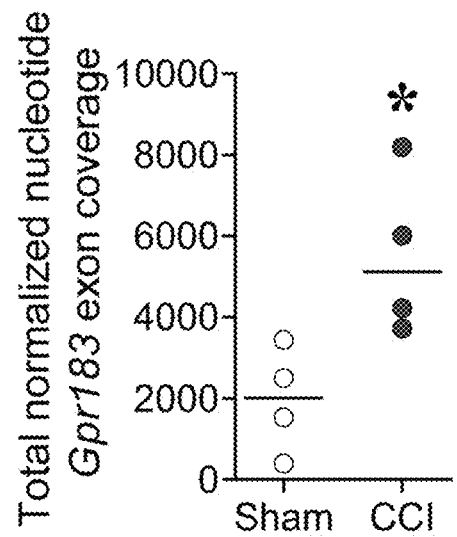
Figure 9C:
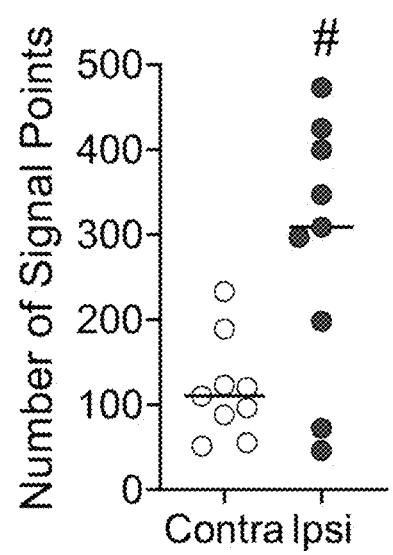
Figure 9D:
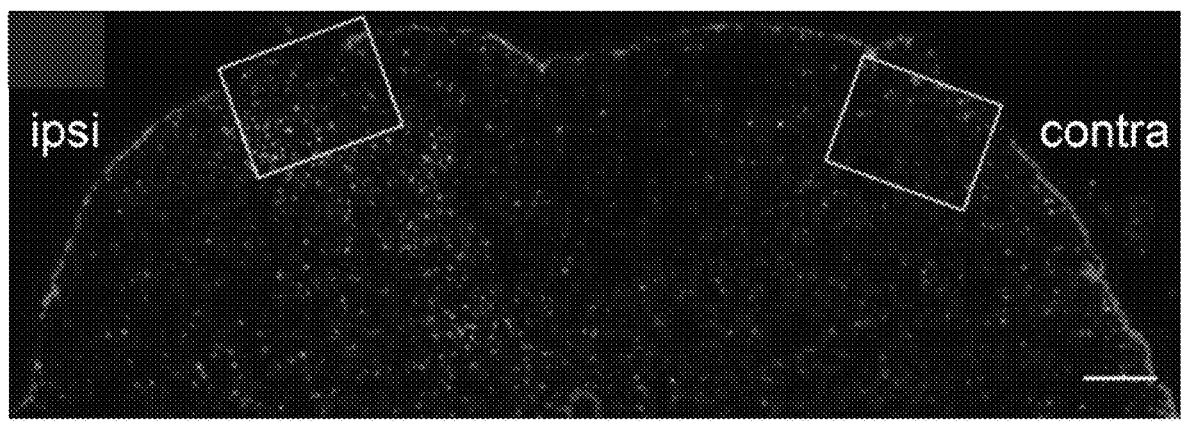
Figures 10A, 10B, 10C:
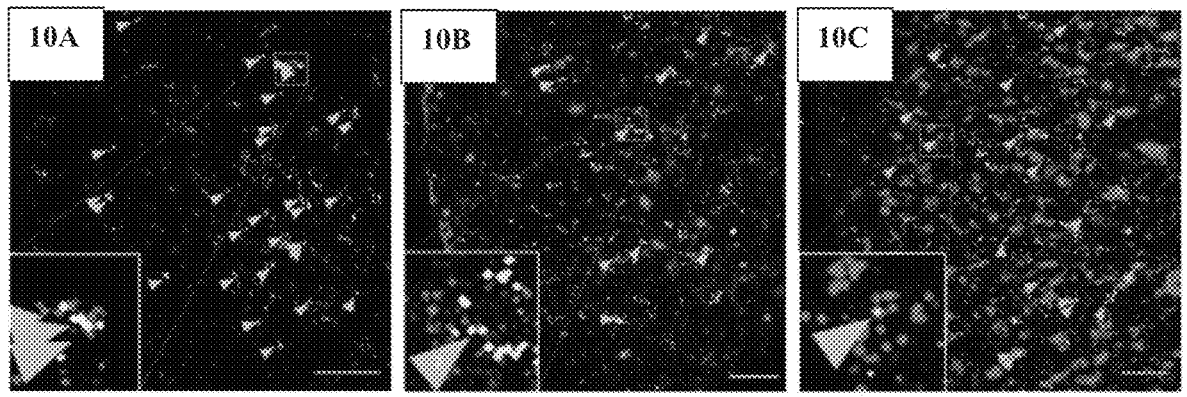
FIGS. 10A-10F depict upregulation of Gpr183 expression in microglia and astrocytes in ipsilateral DH-SC from rats with CCI-induced neuropathic pain.
Figures 10D, 10E, 10F:
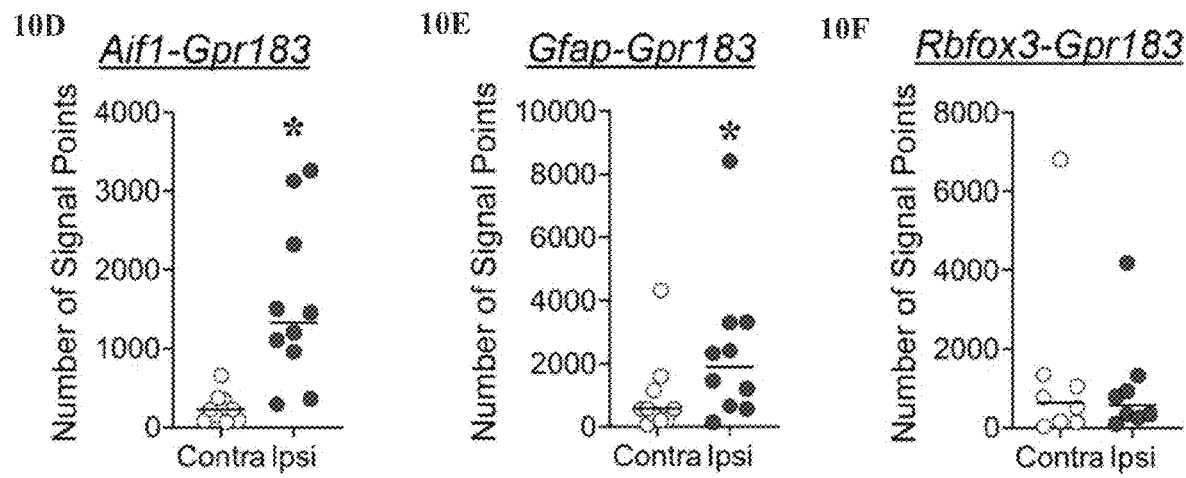

A well-characterized rodent model of neuropathic pain was used. In this model, constriction of the sciatic nerve produced robust mechano-allodynia that peaked within 7-10 days after injury and last for several weeks (Bennett and Xie, 1988). RNA-sequence analysis of dorsal horn spinal cord tissues (DH-SC) harvested at peak mechano-allodynia (D10 after CCI surgery; FIG. 9A) revealed a 2.8-fold ($p=7.59 \times 10^{-14}$, FDR=$9.98 \times 10^{-2}$) increase in Gpr183 expression in the DH-SC from rats with CCI compared to those that received sham surgery (FIG. 9B). To confirm this upregulation and identify where Gpr183 is expressed. RNAscope®-based in situ hybridization was performed in the spinal cord of rats with CCI. Gpr183 was expressed in the dorsal and ventral horn of the spinal cord. However, Gpr83 expression increased 2.4-fold (p=0.024; paired t-test) within lamina and 2 of the DH-SC from mice with CCI ipsilateral to the nerve injury (FIGS. 9C-9D). Further analyses revealed that while Gpr183 co-localized in microglia, astrocytes and neurons (FIG. 10), its expression increased in microglia (6.4-fold; p=0.0021) and astrocytes (2.5-fold; p=0.0021), but not neurons (p=0.4280) (FIG. 10) after CCI surgery.

Oxysterol Metabolism in Spinal Cord after Nerve Injury

Mass spectrometry was performed to quantify the oxysterol content of the spinal cord at different time points after CCI surgery in rats (day 0 pre-surgery, day 5 and day 11 post surgery). 7α,25-OHC was undetected at all time points after CCI surgery (n=8). Its precursor, 25-hydroxycholesterol (25-OHC), was detected, but levels did not change over time (from 0.16 ng/mg, to 0.12 ng/mg and 0.09 ng/mg on day 0, 5 and 11 respectively; one-way ANOVA p=0.0662 for n=8).

Failure of NIBR189 to Inhibit CCI-Induced Mechano-Allodynia

Figure 11:
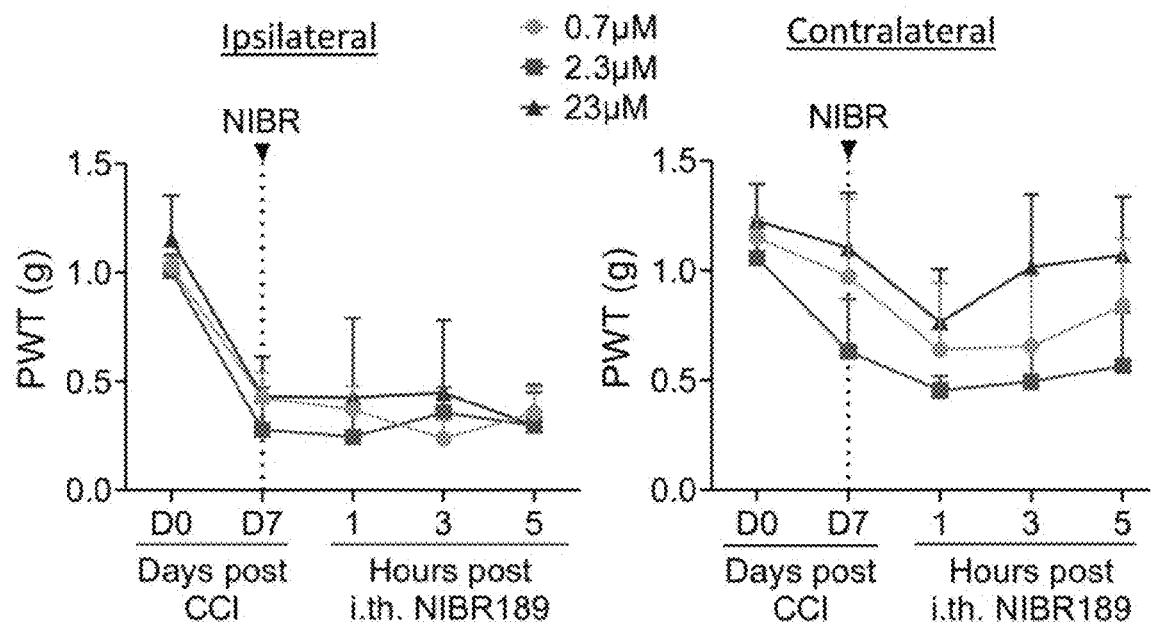
FIG. 11 depicts experiments demonstrating that NIBR189 did not reverse CCI-induced mechanical allodynia. Acute intrathecal injections of NIBR189 (0.7 µM, 2.3 µM n=3; 23 µM; n=4) on D7 post CCI did not reverse mechano-allodynia in male mice. Data are mean±SD; Two-Way ANOVA with Dunnett's multiple comparison; not significant p>0.05 vs D7.

The commercially available small molecule GPR183 antagonists are limited to NIBR189 (IC$_{50}$ 11 nM)(Gessier et al., 2014) and GSK682753A (IC$_{50}$=0.2 μM) (Benned-Jensen et al., 2013). Since GSK682753A has poor microsomal and plasma stability (Ardecky et al., 2010) and is therefore not suitable for in vivo studies, NIBR189 was used to explore the role of GPR183 in nerve-injury induced neuropathic pain. Intrathecal administration of NIBR189 on day 7 after CCI surgery in male mice failed to reverse mechano-allodynia at doses as high as 23 μM (FIG. 11). These doses were selected based on previous literature using NIBR189 in vitro (Gessier et al., 2014; Preuss et al., 2014; Rutkowska et al., 2015). Since information regarding validation of NIBR189 as a specific GPR183 antagonist is limited to the original pharmacological characterization (Gessier et al., 2014), validation of NIBR189 was performed. Validation results demonstrated that NIBR189 was unable to reliably inhibit 7α,25-OHC-induced calcium mobilization; thus, an IC$_{50}$ value for this compound was not obtained. Due to significant variations in dose-responses, single plate IC$_{50}$ values were observed that consistently had standard deviations of multiple magnitudes larger/smaller. This viability was not resolved by different lots or manufacturers of NIBR189, different lots of cells, using different compound vehicles, changes in assay protocols, etc. Importantly, this variability was only observed for NIBR189, and none of the other agonists or antagonists used in the Examples. NIBR189 was previously claimed to be a competitive GPR183 antagonist reported to inhibit 7α,25-OHC binding to GPR183 with an IC$_{50}$ of 11 nM (Gessier et al., 2014). Here, it was found that NIBR189 did not consistently inhibit 7α,25-OHC induced signaling.

Figures 12A, 12B:
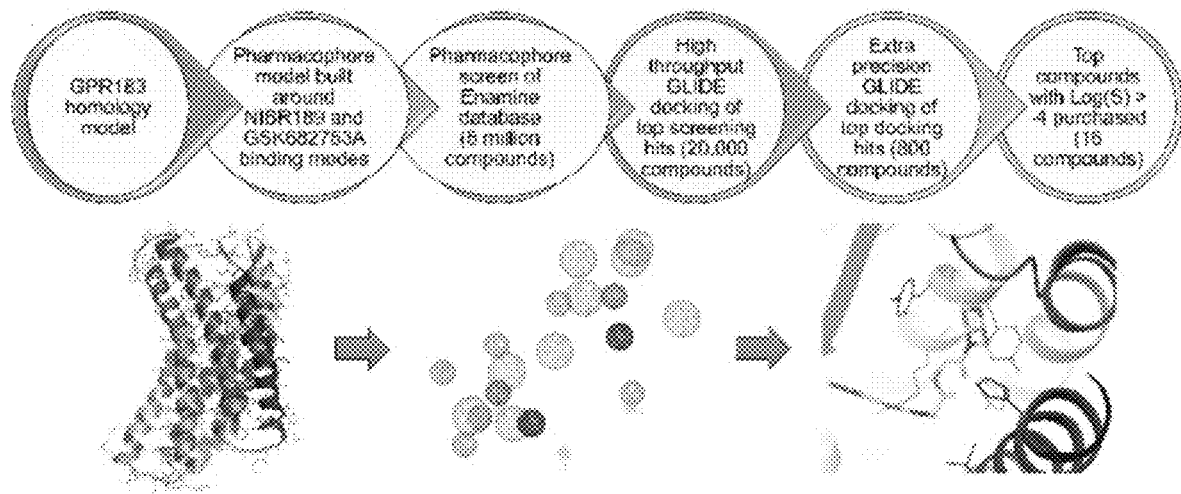
FIGS. 12A-12F depict the inhibition of GPR183-dependent 7α,25-dihydroxycholesterol induced calcium signaling in HL-60 cells using novel GPR183 antagonists.
Figure 12C:
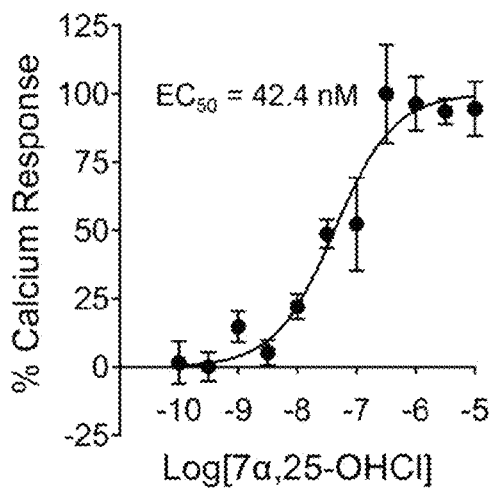
Figure 12D:
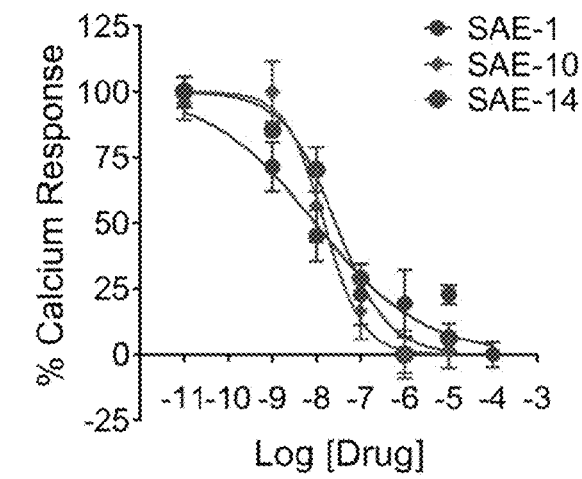
Figure 12E:
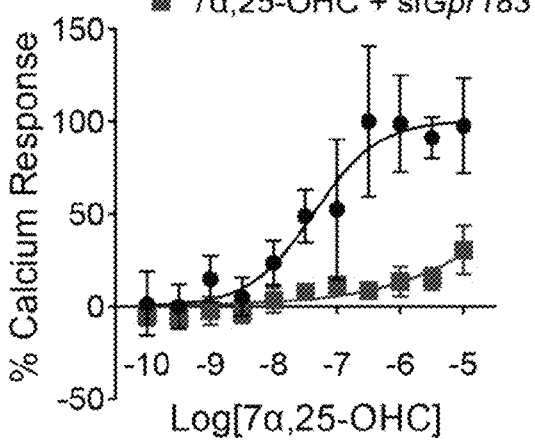
Figure 12F:
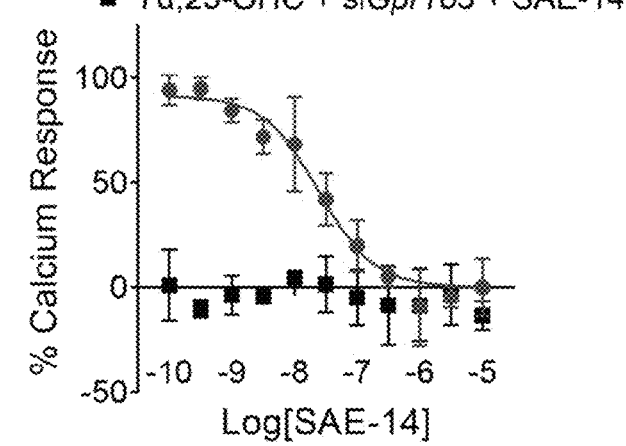

Discovery of Potent and Selective GPR183 Antagonists with Pharmacological Activity NIBR189 and GSK682753A were docked within a GPR183 homology model to build a pharmacophore model. The pharmacophore model based upon the NIBR189-GPR183 and GSK682753A-GPR183 bound structures was built using the automated pharmacophore builder in Schrodinger Phase. This model consisted of aromatic, hydrophobic, H-bond acceptor/donator, and size exclusion spheres in 3-dimensional space describing the key features needed for binding to GPR183 by those two compounds. Using an in silico approach, a library of 5 million compounds was screened for similarity to the GPR183 pharmacophore model. Compounds with the highest similarity scores were docked and ranked based upon their thermodynamics of binding (FIG. 12A). The top 16 commercially available compounds were purchased and then tested for GPR183-specific agonism and antagonism in a calcium mobilization assay (FIGS. 12B-12D). Three of those compounds were able to antagonize 7α,25-OHC-induced calcium mobilization with IC$_{50}$ values below 50 nM (FIGS. 12, 12D). These compounds were unable to effect calcium mobilization in the HL-60 cells on their own. Results were confirmed to be GPR183-specific using siRNA to block protein expression. In these studies, 7α,25-OHC-induced calcium mobilization (FIG. 12E), and GPR183 antagonism (FIG. 12F) were both abolished using GPR83-specific siRNA.

GPR183 Antagonists Reversed CCI-Induced Mechanical Allodynia

Figure 13:
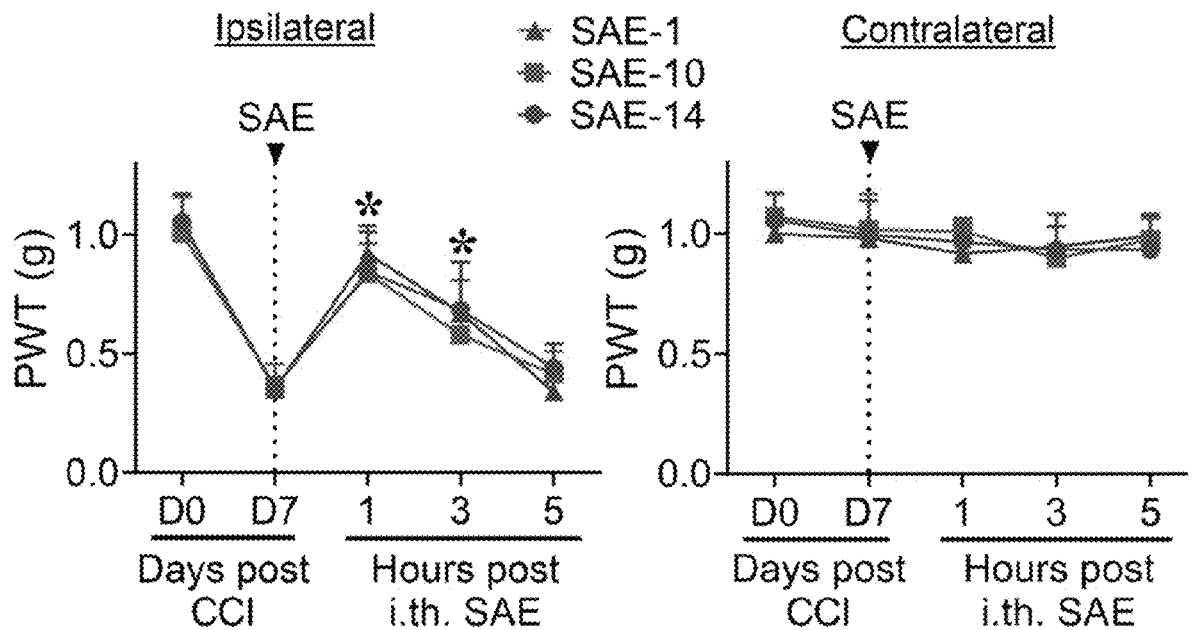
FIG. 13 depicts reversal of nerve injury-induced allodynia in mice using GPR183 antagonists. Acute intrathecal injections of SAE-1 (800 nM), SAE-10 (1.4 µM), or SAE-14 (2.9 µM) reversed CCI-induced mechano-allodynia on D7 post-surgery in male and female mice (data combined). Data are mean±SD for n=4 per group; Two-Way ANOVA with Dunnett's multiple comparison *p<0.05 vs D7.

Using the lead compounds, whether GPR183 was functionally involved in neuropathic pain states was assed. When administered in vivo to mice the GPR83 antagonists (designated SAE-1, SAE-10, and SAE-14) reversed CCI-induced mechanical allodynia in a time-dependent manner (FIG. 13). For in vivo studies the concentration was increased to 100× the in vitro IC$_{50}$ of these compounds.

GPR183 Signaling in Naïve Animals was Pro-Nociceptive

Figures 14A, 14B:
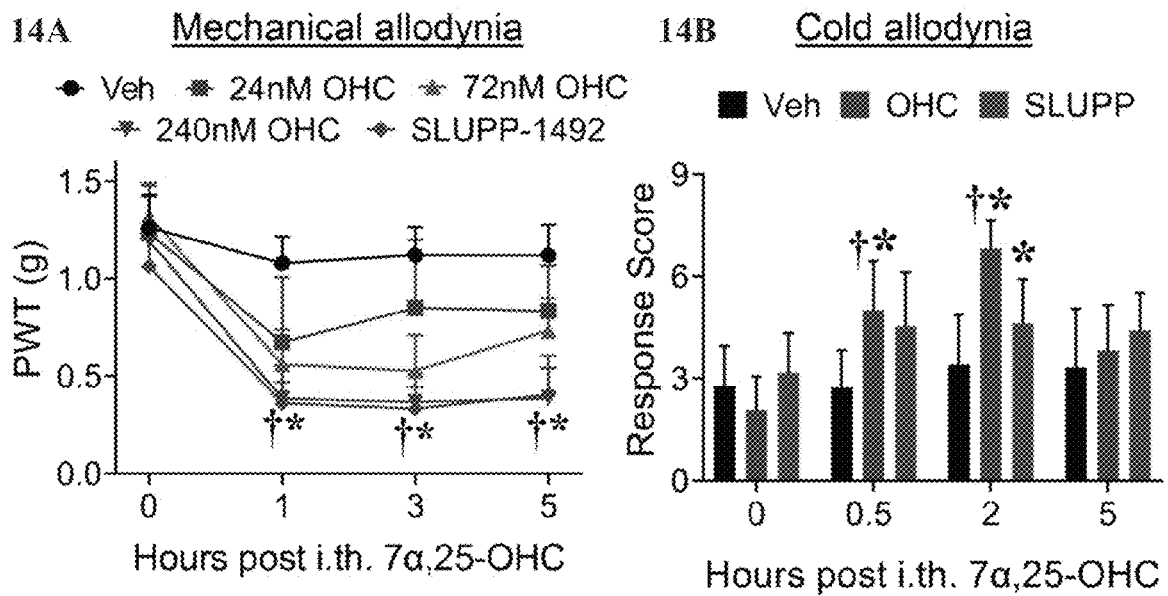
FIGS. 14A-14D depict intrathecal administration of 7α,25-dihydroxycholesterol and its analog induced allodynia in mice.
Figures 14C, 14D:
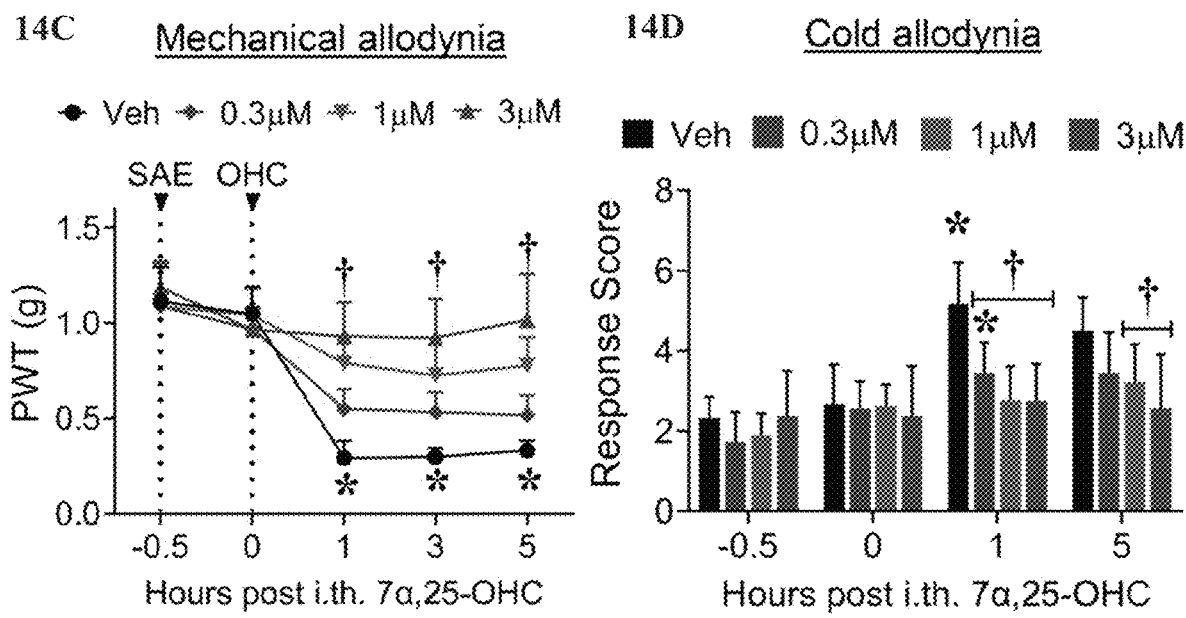

Results using GPR183 antagonists in neuropathic pain models indicated that GPR183 signaling in the spinal cord contributed to the maintenance of neuropathic pain. I.th. injections of 7α,25-OHC in mice induced a dose and time-dependent mechano-allodynia (ED$_{50}$=74 nM; FIG. 14A) and cold allodynia (FIG. 14B). Additionally, a fluorinated analog of 7α,25-OHC, designated SLUPP-1492, induced similar results (FIGS. 14A-14B). Pre-treatment with one of the novel GPR183 antagonists (SAE-14) blocked these effects of 7α,25-OHC in a dose-dependent manner (FIGS. 14C-14D).

SLUPP-1492 Synthesis

25-Hydroxycholesterol 3β-acetate (SLUPP-1828)

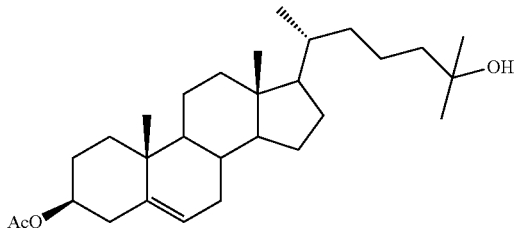 [SMILES: CC(=O)O[C@H]1CC[C@@]2(C)C(=CCC3C4CCC([C@H](C)CCCC(C)(C)O)[C@@]4(C)CCC32)C1]

To a solution of 25-hydroxycholesterol (1,430 mg, 1.068 mmol), triethylamine (0.357 mL, 2.563 mmol) and acetic anhydride (0.122 mL, 1.281 mmol) in THF (10 mL) was added catalytic amount of 4-Dimethylaminopyridine (DMAP) (20-30 mg) at room temperature. The reaction was stirred for 20 h and quenched with saturated solution of NH$_4$Cl in water and extracted with dichloromethane. The organic layer was combined and dried over Na$_2$SO$_4$. After filtration, the solvent was removed under reduced pressure and purified using flash chromatography (petroleum ether/diethyl ether, 1:1) on silica gel. The residue was obtained as pure white powder 25-Hydroxycholesterol 3β-acetate (2, 409 mg, 86%). $^1$H NMR (400 MHz, CDCl3) δ 5.37 (d, J=4.9 Hz, 1H), 4.66-4.55 (m, 1H), 2.32 (d, J=7.2 Hz, 2H), 2.03 (s, 3H), 2.01-1.92 (m, 2H), 1.90-1.78 (m, 3H), 1.57 (s, 6H), 1.52-1.34 (m, 8H), 1.21 (s, 8H), 1.18-1.04 (m, 5H), 1.02 (s, 4H), 0.93 (d, J=6.5 Hz, 3H), 0.68 (s, 3H), LC-MS: found [(M-AcOH)$^+$] m/z=385.3, expected (m/z=385.3).

(3β)-3-(Acetyloxy)-25-hydroxycholest-5-en-7-one
(SLUPP-1829)

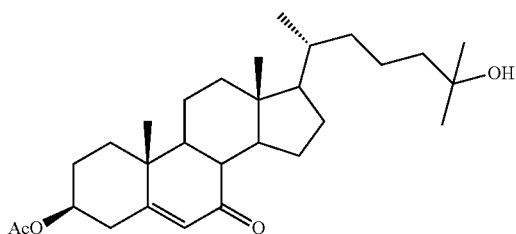 [SMILES: CC(=O)O[C@H]1CC[C@@]2(C)C(=CC(=O)C3C4CCC([C@H](C)CCCC(C)(C)O)[C@@]4(C)CCC32)C1]

To a solution of 25-Hydroxycholesterol 3β-acetate (2, 409 mg, 0.9 mmol) in ethyl acetate (15 mL) and molecular sieves (4A) was added t-butylhydroperoxide (0.8 mL, 5 mmol) and stirred under nitrogen for 20 min. To the reaction mixture, manganese acetate (25 mg, 0.09 mmol) was added and stirred at room temperature for 48 h. The solids were filtered off through a pad of celite. The solvent was removed under reduced pressure and purified using flash Chromatography (petroleum ether/diethyl ether, 1:2) on silica gel. The residue was obtained pure white powder (3β)-3-(Acetyloxy)-25-hydroxycholest-5-en-7-one (3, 248 mg, 59%). 1H NMR (400 MHz, C6D6) δ 5.73 (d, J=1.7 Hz, 1H), 4.75-4.65 (m, 1H), 3.04-2.93 (m, 1H), 2.34-2.26 (m, 1H), 2.16 (s, 1H), 2.08-1.90 (m, 3H), 1.83-1.75 (m, 1H), 1.73 (s, 3H), 1.54-1.28 (m, 11H), 1.26-1.17 (m, 3H), 1.15-1.05 (m, 2H), 1.10 (s, 6H), 1.02 (d, J=6.5 Hz, 3H), 0.99-0.94 (m, 1H), 0.74 (s, 3H), 0.71-0.65 (m, 1H), 0.61 (s, 3H).). LC-MS: found [(M-AcOH)+] m/z=399.3, expected (m/z=399.3).

Cholestene-7β-trifluoromethyl, 3β, 7α, 25-triol
(SLUPP-1492, 5)

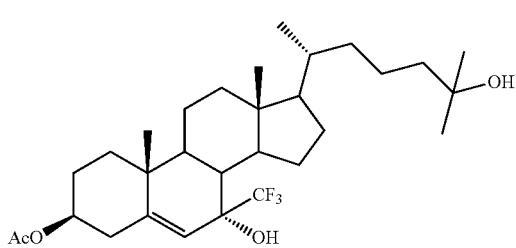 [SMILES: CC(=O)O[C@H]1CC[C@@]2(C)C(=C[C@](O)(C(F)(F)F)C3C4CCC([C@H](C)CCCC(C)(C)O)[C@@]4(C)CCC32)C1]

To a solution of the above acetate (0.247 g, 0.539 mmol) in DME (2.0 mL) was added cesium fluoride (8 mg, 0.054 mmol) and then a DME (0.25 mL) solution of trifluoromethyl trimethylsilane (0.169 g, 1.19 mmol)). The resulting mixture was stirred for 2 days at room temperature after which the reaction was concentrated to dryness. The resulting residue was taken up in 1% EtOAc-hexanes and subjected to flash chromatography, Elution with EtOAc-Hexanes (1% to 5% to 20%) led to isolation (0.191 g, 0.36 mmol) of a glassy solid that appears to be 25-trimethylsiloxy starting material. This material was re-subjected to the trifluoromethylation conditions as described below.

The material isolated from above (0.191 g, 0.36 mmol) was dissolved in DME (1.0 mL) and stirred at room temperature. To this mixture was added cesium fluoride (5 mg, 0.04 mmol) followed by addition of a DME (0.5 mL) solution of trifluoromethyl trimethylsilane (0.113 g, 0.792 mmol). The reaction was stirred at room temperature for 24 h. Some starting material remained so additional trifluormethyl trimethylsilane (0.051 g, 0.360 mmol) was added and the reaction and was stirred for another 24 h. The reaction was judged complete by thin-layer chromatography (TLC) and the reaction was concentrated to dryness. The resulting residue was dissolved in 1% EtOAc-Hexanes and purified by flash chromatography. Elution with EtOAc-hexanes (1% to 10%) led to the isolation (0.223 mg) of a complex mixture of mono- and bis-silylated products with incorporation of the trifluoromethyl group.

The above mixture was dissolved in MeOH (3 mL) and to this was added potassium carbonate (0.154, 1.1 mmol) and the mixture was stirred at room temperature. The solution turned pale yellow upon addition of the potassium carbonate. The reaction was allowed to stir overnight at room temperature. The reaction was judged complete by TLC and the reaction was filtered through a small pad of celite washing with MeOH and then EtOAc. The organics were combined and concentrated. The residue was dissolved in small amount of MeOH and absorbed onto silica and purified by flash chromatography. Elution with EtOAc-hexanes (5-50%) led to isolation of the desired product (0.066 g) as mixture of diastereomers. The material was dried overnight under vacuum in a 1-dram vial. The resulting residue was dissolved in hot EtOAc and the vial was then allowed to cool to room temperature. After ~1 h a precipitate resulted. The EtOAc was carefully removed and the resulting solid was washed with cold EtOAc and filtered to give the desired product (0.025 g) in >90% purity as a white crystalline solid. H NMR (400 MHz, CDCl$_3$) δ 5.31 (s, 1H), 3.55 (s, 1H), 2.48-2.37 (m, 1H), 2.30-2.19 (m, 1H), 2.04-1.84 (m, 5H), 1.67-1.58 (m, 11H), 1.56-1.47 (m, 5H), 1.46-1.32 (m, 7H), 1.29-1.15 (m, 11H), 1.15-1.01 (m, 5H), 0.98-0.89 (m, 6H), 0.72 (s, 3H), LC-MS, found [M+Na] m/z=0.15-1.01 (m, 5H), 0.98-0.89 (m, 6H), 0.72 (s, 3H), LC-MS, found [M+Na] m/z=509.3 (expected m/z=509.3) and [(M+H)−2H$_2$O] m/z=451.3 (expected 451.3).

Figure 15:
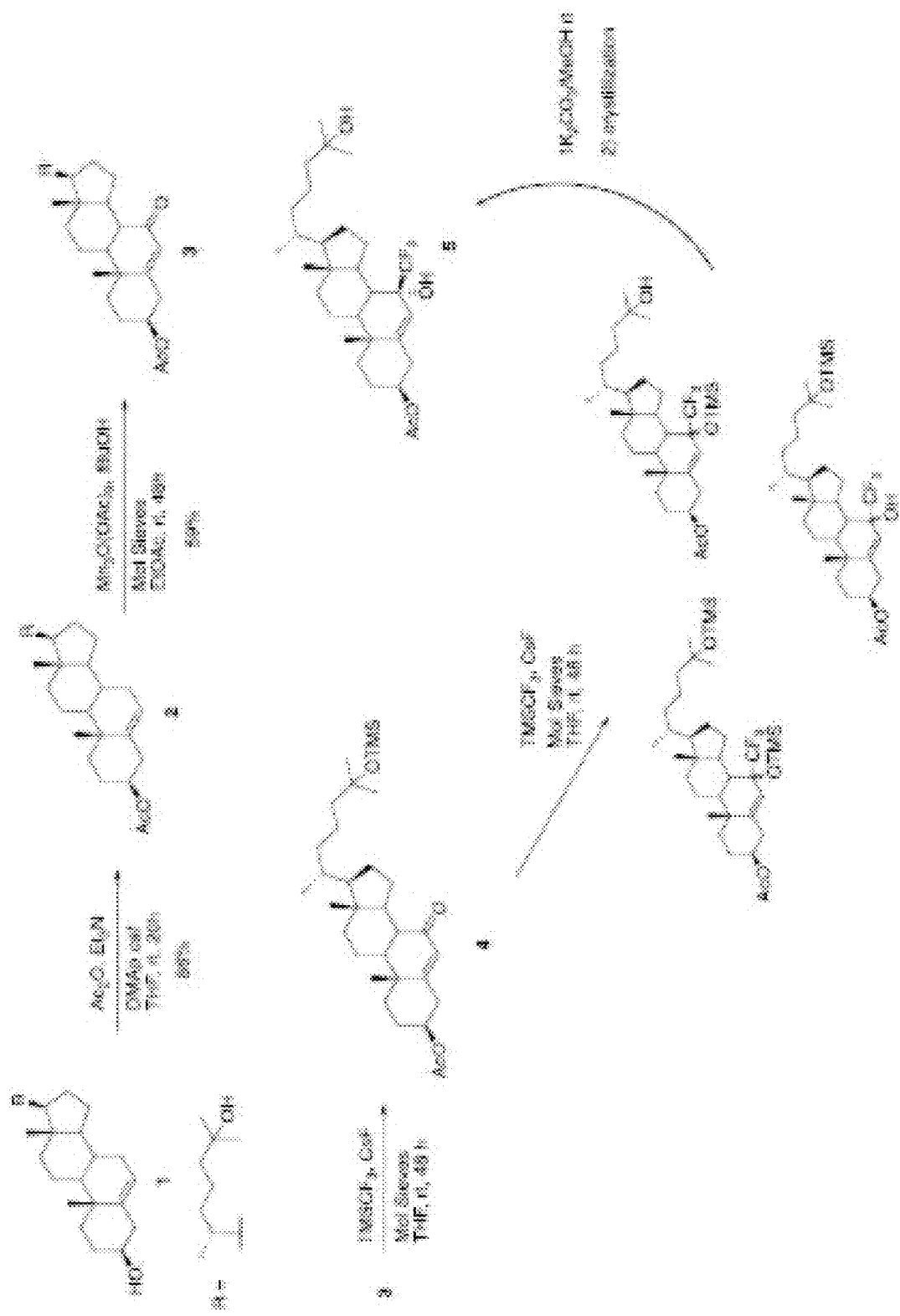
FIG. 15 is a schematic depicting the reaction scheme to prepare SLUPP-1492

FIG. 15 depicts the reaction scheme discussed above to prepare SLUPP-1492.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a". "an", "the" and "said" are intended to mean that there are one or more of the elements. The terms "comprising", "including" and "having" are intended to be inclusive and mean that there may be additional elements other than the listed elements.

What is claimed is:

1. A compound having a structure selected from the group consisting of:

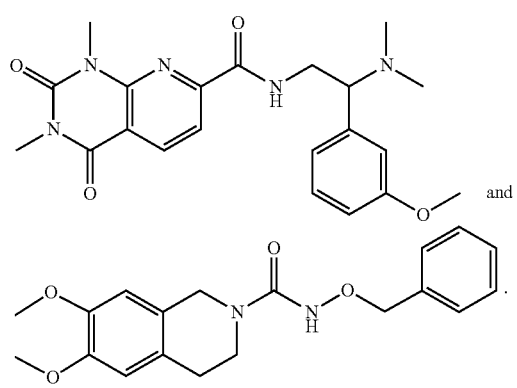

2. A compound having a structure selected from the group consisting of:

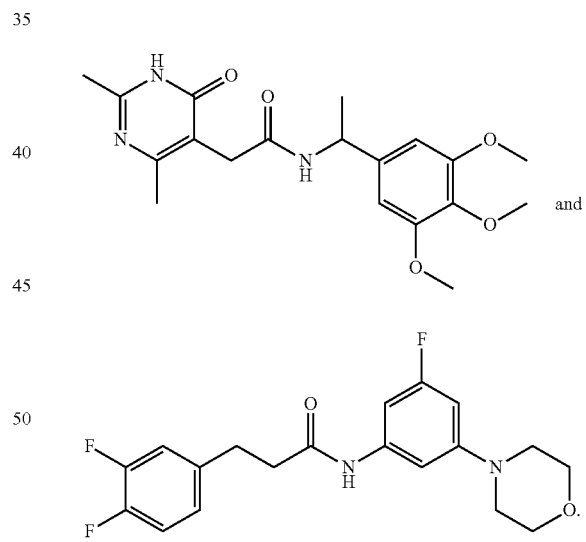

* * * * *